(12) United States Patent
Zhao et al.

(10) Patent No.: US 10,514,354 B2
(45) Date of Patent: Dec. 24, 2019

(54) BIOSENSOR STRUCTURES FOR IMPROVED POINT OF CARE TESTING AND METHODS OF MANUFACTURE THEREOF

(71) Applicant: Abbott Point of Care Inc., Princeton, NJ (US)

(72) Inventors: Tian-Xian Zhao, Ottawa (CA); Glenn Martin, Ottawa (CA); Kenneth Hardage, Ottawa (CA); Steven R. Breeze, Ottawa (CA); Stephen Snyder, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 384 days.

(21) Appl. No.: 15/285,687

(22) Filed: Oct. 5, 2016

(65) Prior Publication Data

US 2017/0023514 A1    Jan. 26, 2017

Related U.S. Application Data

(62) Division of application No. 14/206,636, filed on Mar. 12, 2014, now Pat. No. 9,487,811.
(Continued)

(51) Int. Cl.
*G01N 27/327*    (2006.01)
*C12Q 1/00*    (2006.01)
(Continued)

(52) U.S. Cl.
CPC ......... *G01N 27/3271* (2013.01); *C12Q 1/005* (2013.01); *C23C 14/34* (2013.01);
(Continued)

(58) Field of Classification Search
CPC .............................. G01N 27/3271; H01M 4/90
See application file for complete search history.

(56) References Cited

U.S. PATENT DOCUMENTS

| 4,954,087 A | 9/1990 | Lauks et al. |
| 5,096,669 A | 3/1992 | Lauks et al. |

(Continued)

FOREIGN PATENT DOCUMENTS

| WO | 1999/38003 A1 | 7/1999 | |
| WO | WO-9938003 A1 * | 7/1999 | ............. C12Q 1/002 |
| WO | 2014/150876 A2 | 9/2014 | |

OTHER PUBLICATIONS

Final Office Action issued in U.S. Appl. No. 14/206,636, dated Apr. 12, 2016, 6 pages.
(Continued)

*Primary Examiner* — Dah-Wei D. Yuan
*Assistant Examiner* — Andrew J Bowman
(74) *Attorney, Agent, or Firm* — Kilpatrick Townsend & Stockton LLP

(57) ABSTRACT

The present invention relates to analytical testing devices and methods for fabricating electrochemical creatinine biosensors, and in particular using point of care electrochemical biosensors for testing for creatinine in samples. For example, the present invention may be directed to a biosensor having an electrode, a first printed layer formed on the electrode and having a first matrix that includes creatinine amidohydrolase (CNH), creatine amidinohydrolase (CRH), and sarcosine oxidase (SOX), and second printed layer formed over the first printed layer and having a second matrix that includes CRH, SOX, and catalase.

14 Claims, 25 Drawing Sheets

Related U.S. Application Data

(60) Provisional application No. 61/790,078, filed on Mar. 15, 2013.

(51) Int. Cl.
*C23C 14/34* (2006.01)
*C23C 14/58* (2006.01)
*C25D 5/48* (2006.01)
*C25D 7/00* (2006.01)

(52) U.S. Cl.
CPC .............. *C23C 14/58* (2013.01); *C25D 5/48* (2013.01); *C25D 7/00* (2013.01)

(56) References Cited

U.S. PATENT DOCUMENTS

| | | |
|---|---|---|
| 5,200,051 A | 4/1993 | Cozzette et al. |
| 5,514,253 A | 5/1996 | Davis et al. |
| 5,536,472 A | 9/1996 | Terashima et al. |
| 5,821,399 A | 10/1998 | Zelin |
| 6,030,827 A | 2/2000 | Davis et al. |
| 7,682,833 B2 | 3/2010 | Miller et al. |
| 2006/0275860 A1 | 12/2006 | Kjaer et al. |
| 2007/0034512 A1* | 2/2007 | Yamaoka ............ C12Q 1/004 204/403.01 |
| 2007/0158213 A1 | 7/2007 | Hsiung et al. |
| 2013/0343955 A1 | 12/2013 | Doyle et al. |
| 2014/0262777 A1 | 9/2014 | Zhao et al. |

OTHER PUBLICATIONS

Non-Final Office Action issued in U.S. Appl. No. 14/206,636, dated Dec. 23, 2015, 11 pages.

Notice of Allowance issued in U.S. Appl. No. 14/206,636, dated Jul. 20, 2016, 7 pages.

Madaras et al., "Microfabricared amperometric creatine and creatinine biosensors", *Anal Chim Acta* 319, pp. 335-345, 1996.

Berberich et al., "A stable three-enzyme creatinine biosensor. 3. Immobilization of creatinine amidohydrolase and sensor development", *Acta Biomaterialia* 1, pp. 193-199, 2005.

Killard, et al. "Creatinine biosensors: principles and designs", *Trends in Biotechnology*, Elsevier Science Ltd. Publications, Cambridge, GB, vol. 18, No. 10, pp. 433-437, Oct. 2000.

Mohabbati-Kalejahi, et al. "A review on creatinine measurement techniques", *Talanta*, Elsevier B.V., Amsterday, NL, vol. 97, pp. 1-8, Apr. 2012.

International Search Report and Written Opinion dated Dec. 1, 2014 in International Patent Application No. PCT/US2014/024439, 18 pages.

\* cited by examiner

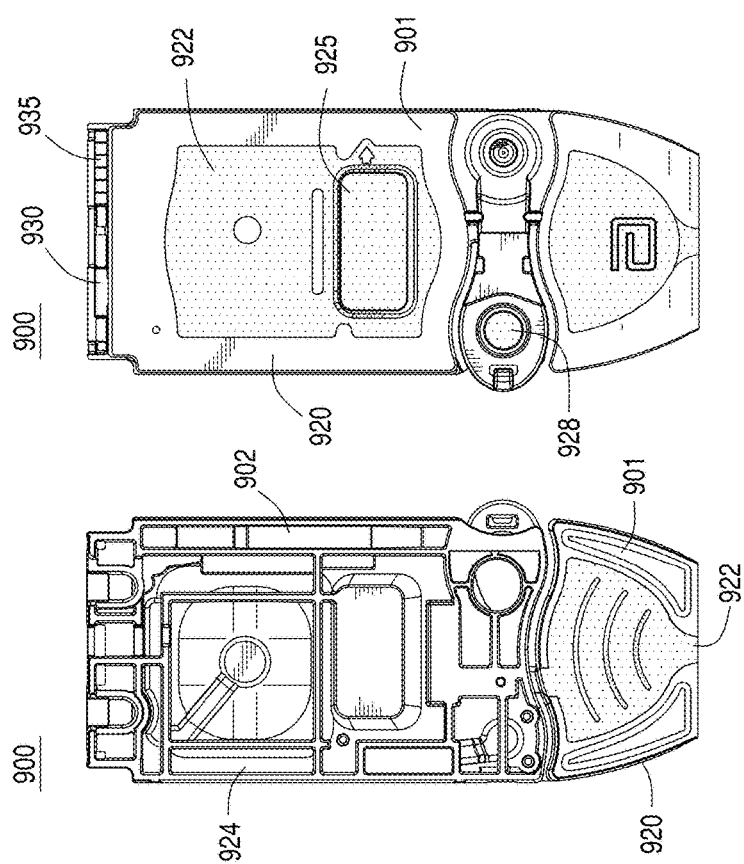
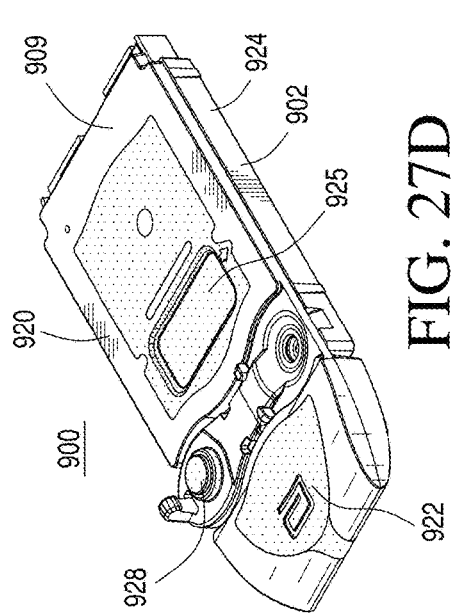
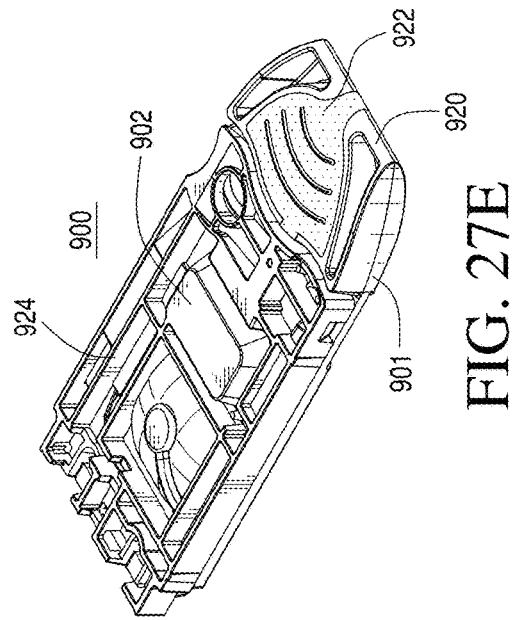
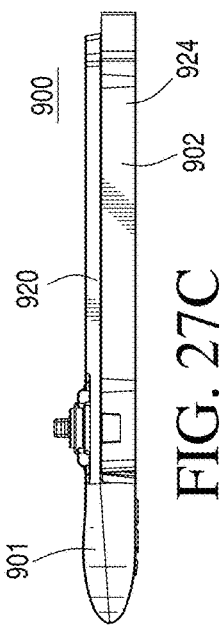

BIOSENSOR STRUCTURES FOR IMPROVED POINT OF CARE TESTING AND METHODS OF MANUFACTURE THEREOF

CROSS REFERENCE TO RELATED APPLICATIONS

This application is a divisional application of U.S. patent application Ser. No. 14/206,636 filed on Mar. 12, 2014, which claims priority to U.S. Provisional Application No. 61/790,078 filed on Mar. 15, 2013, the entireties of which are incorporated herein by reference.

FIELD OF THE INVENTION

The present invention relates to analytical testing devices comprising electrochemical biosensors and methods for fabricating the electrochemical biosensors. Specifically, the present invention relates to analytical testing devices comprising electrochemical creatinine biosensors and methods for fabricating the electrochemical creatinine biosensors, and in particular using point of care electrochemical biosensors for testing for creatinine in samples.

BACKGROUND OF THE INVENTION

A biosensor is a device for measuring the concentration of an analyte in a biological sample. A typical biosensor comprises a sensitive biological recognition element able to interact specifically with a target analyte, and a transducer or detector element that is able to transform the recognition event of the analyte with the biological element into a measurable signal. In contrast with conventional bioassays, biosensors allow the detection of molecular interactions as they take place, without requiring auxiliary procedures, making them highly attractive for biotechnological applications.

Among the various types of biosensors, electrochemical biosensors are typically based on enzymatic catalysis of a reaction that produces or consumes electrons. The biosensor substrate usually contains three electrodes: a reference electrode, a working electrode and a counter electrode. The target analyte is typically involved in a reaction that takes place on the working electrode surface, and the reaction may cause either electron transfer across a double layer (producing a current) or can contribute to a double layer potential (producing a voltage).

One such target analyte typically detected using electrochemical biosensors is creatinine. Creatinine is the end metabolite within the human body when creatine becomes creatine phosphate and is used as an energy source for muscle contraction. The creatinine produced is filtered by the kidney glomeruli and then excreted into the urine without reabsorption. The determination of creatinine in body fluids is useful for diagnosing muscle diseases or various kidney diseases such as nephritis and renal insufficiency.

Typically, in order to detect creatinine using an electrochemical biosensor the creatinine needs to be reduced to a detectable product such as hydrogen peroxide. One such pathway for achieving a detectable product includes the enzyme cascade comprising three enzymes (i) creatinine amidohydrolase (CNH) or creatininease, (ii) creatine amidinohydrolase (CRH) or creatinase, and (iii) sarcosine oxidase (SOX). More specifically, the cascade includes using creatinine amidohydrolase to catalyze the hydrolysis of creatinine to creatine. Thereafter, creatine amidinohydrolase may be used to catalyze the hydrolysis of creatine to sarcosine and urea. Finally, sarcosine oxidase may be used to catalyze the oxidative demethylation of sarcosine to yield glycine and detectable hydrogen peroxide. However, as there is a significant concentration of endogenous creatine in the blood, the endogenous creatine significantly effects the determined concentration of creatinine because it is an intermediary byproduct of the enzyme cascade used to detect the creatinine. In other words, the endogenous creatine causes interference with the detection of creatinine in the sample because the endogenous creatine is also reduced to the product hydrogen peroxide via the use of creatine amidinohydrolase and sarcosine oxidase.

Accordingly, to overcome the influence of endogenous creatine on the biosensor, a screening layer containing the enzymes creatine amidinohydrolase, sarcosine oxidase, and catalase may be used to reduce the concentration of the endogenous creatine in the sample. For example, a typical creatinine biosensor may use a double layer deposited over a sensor. One layer may be used to enzymatically convert the creatinine to detectable hydrogen peroxide in an enzyme cascade such as the one described above. The other layer may be used as the screening layer to enzymatically remove the endogenous creatine using an enzyme cascade such as the one described above.

Biosensors comprising the aforementioned screening layer typically have a high design complexity and expensive fabrication techniques. Accordingly, the need exists for improved biosensor designs that addresses endogenous creatine interference and for improved processes for making such biosensors.

SUMMARY OF THE INVENTION

In one embodiment, the present invention is a biosensor including an electrode, a first printed layer formed on the electrode comprising a first matrix that includes CNH, CRH, and SOX, and a second printed layer formed over the first printed layer comprising a second matrix that includes CRH, SOX, and catalase.

In some aspects, the biosensor further comprises a third printed layer formed on the first printed layer such that the third printed layer is disposed between the first printed layer and the second printed layer, the third printed layer comprising a third matrix that includes CRH.

In some embodiments, the biosensor further comprises a fourth printed layer formed on the second printed layer comprising a fourth matrix that includes CRH, SOX, and catalase.

In another embodiment, the present invention is a method of manufacturing a biosensor comprising forming an electrode on a wafer, microdispensing a first layer on the electrode comprising a first matrix that includes CNH, CRH, and SOX, and microdispensing a second layer over the first layer comprising a second matrix that includes CRH, SOX, and catalase.

In another embodiment, the present invention is a biosensor comprising an electrode and a first spun layer formed on the electrode comprising a first aqueous polymeric matrix having at least one enzyme. The first spun layer may have a thickness in a range of about 2-5 μm. The biosensor may further comprise a second spun layer formed over the first spun layer comprising a second aqueous polymeric matrix having at least one enzyme. The second spun layer may have a thickness in a range of about 10-20 μm.

In some aspects, the biosensor further comprises a third spun layer formed on the first spun layer such that the third spun layer is disposed between the first spun layer and the second spun layer. In some embodiments, the third spun layer may comprise a third aqueous polymeric matrix having at least one enzyme, and the third spun layer may have a thickness in a range of about 2-5 µm.

In some embodiments, the biosensor further comprises a silane layer formed on the electrode such that the silane layer is disposed between the electrode and the first spun layer.

In yet another embodiment, the present invention is directed to a method of manufacturing a biosensor comprising forming an electrode on a wafer and spin coating a first layer on the electrode comprising a first aqueous polymeric matrix having at least one enzyme. The first layer may have a thickness in a range of about 2-5 µm. The method may further comprise spin coating a second layer over the first layer comprising a second aqueous polymeric matrix having at least one enzyme. The second layer may have a thickness in a range of about 10-20 µm.

BRIEF DESCRIPTION OF THE DRAWINGS

The present invention will be better understood in view of the following non-limiting figures, in which:

FIGS. 27A-27E show top, bottom, side, and perspective views of a cartridge in a closed position in accordance with some aspects of the invention.

DETAILED DESCRIPTION OF THE INVENTION

Introduction

The present invention relates to analytical testing devices comprising electrochemical biosensors and methods for fabricating the electrochemical biosensors. Specifically, the present invention relates to analytical testing devices comprising electrochemical creatinine biosensors and methods for fabricating the electrochemical creatinine biosensors, and in particular using point of care electrochemical biosensors for testing for creatinine in samples. In some embodiments, the invention relates to methods of fabricating biosensor structures on chips such that the biosensors operate in a vertical manner and each biosensor comprises a number of biolayers fabricated at various thicknesses for efficiently and effectively attenuating interferents (e.g., creatine) and detecting target analytes (e.g., creatinine). Accordingly, the present invention provides biosensor structures and methods of manufacturing that advantageously provide for improved chemical removal of creatine interference.

More specifically, the present invention may be directed to a method of microdispensing (e.g., printing) enzyme-biolayer matrixes onto a substrate, and the resultant biosensor structures. Advantageously, the microdispensing processes described herein overcome waste and cost problems associated with traditional spin coating enzyme-biolayer matrixes onto a substrate. For example, traditional spin coating processes waste a large amount of costly enzyme during the film forming process, whereas the manufacture of a biosensor using the microdispensing embodiments of the present invention may provide significant cost savings over traditional spin coating processes because the enzyme-biolayer matrix is drop dispensed using controlled volumes. Advantageously, the drop dispensing wastes very little if any enzyme-biolayer matrix.

Additionally, the present invention may be directed to alternative methods of spin coating enzyme-biolayer matrixes onto a substrate, and the resultant biosensor structures. Advantageously, the spin coating processes described herein overcome layer thickness problems associated with traditional spin coating enzyme-biolayer matrixes onto a substrate. For example, traditional spin coating processes only produce layers of consistent thickness across a substrate up to about 5 microns, whereas the manufacture of a biosensor using the spin coating embodiments of the present invention provide a means for forming biolayers of up to unexpected ten-fold greater thickness using combinations of spinning and drying techniques not used previously. Advantageously, this is important for the manufacture of biosensors that are consistent across a wafer and from wafer to wafer. It is also important for delivering a screening layer that eliminates interfering substances, e.g., creatine in a creatinine sensor.

Overview of Biosensor Fabrication

Figure 1:
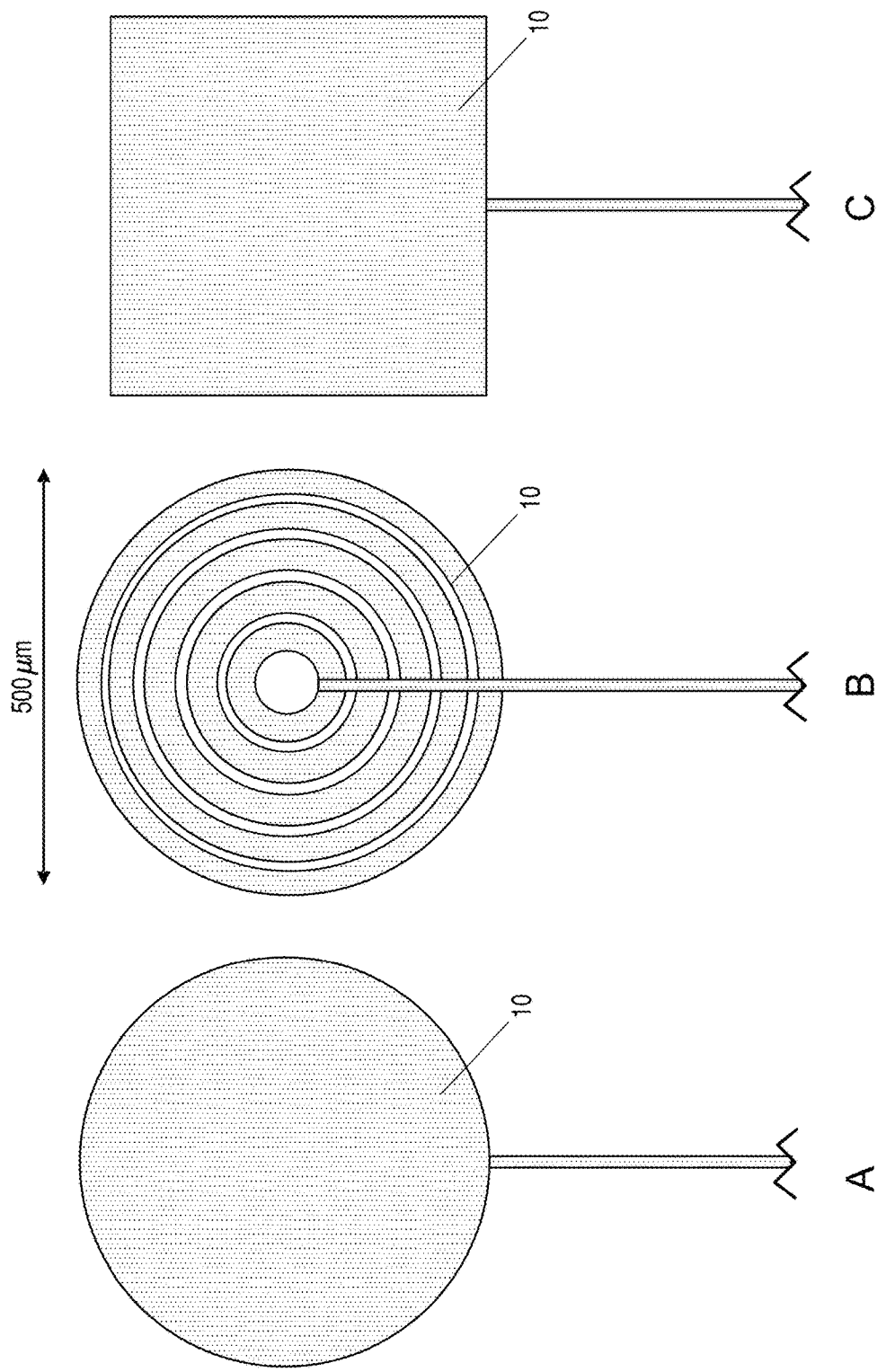
FIG. 1 shows a number of working electrode designs in accordance with some aspects of the invention.
Figure 2:
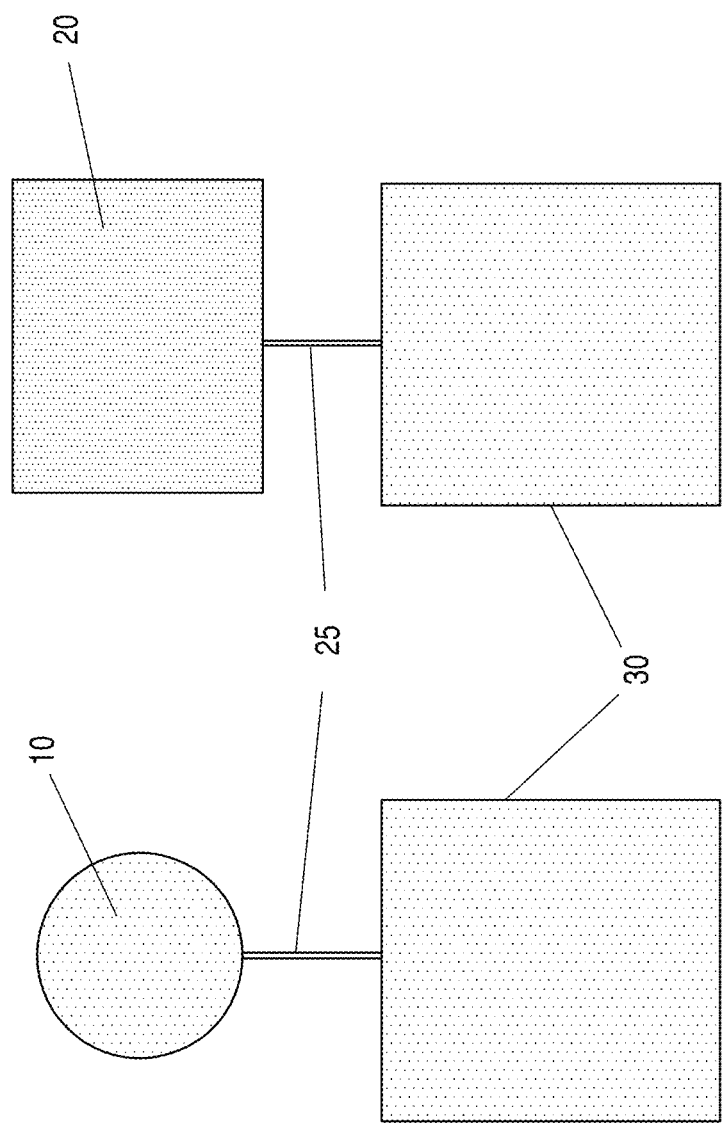
FIG. 2 shows an electrochemical cell comprising a working electrode and reference/counter electrodes in accordance with some aspects of the invention.

FIGS. 1 and 2 show an enzyme biosensor provided as a unit cell comprising a catalytic working electrode 10 and a combined reference and counter electrode 20 in accordance with some aspects of the present invention. The working electrode 10 and counter electrode 20 may be connected by a lead or signal line 25 (e.g., an over-passivated signal line) to respective contact pads 30. The unit cell may be composed of a single unit cell confined within a rectangular area which is repeated in a square array several hundred times on a single substrate, for example, a silicon wafer, or composed of two separate unit cells that are grouped together to make a final device comprising the enzyme biosensor.

Figure 3:
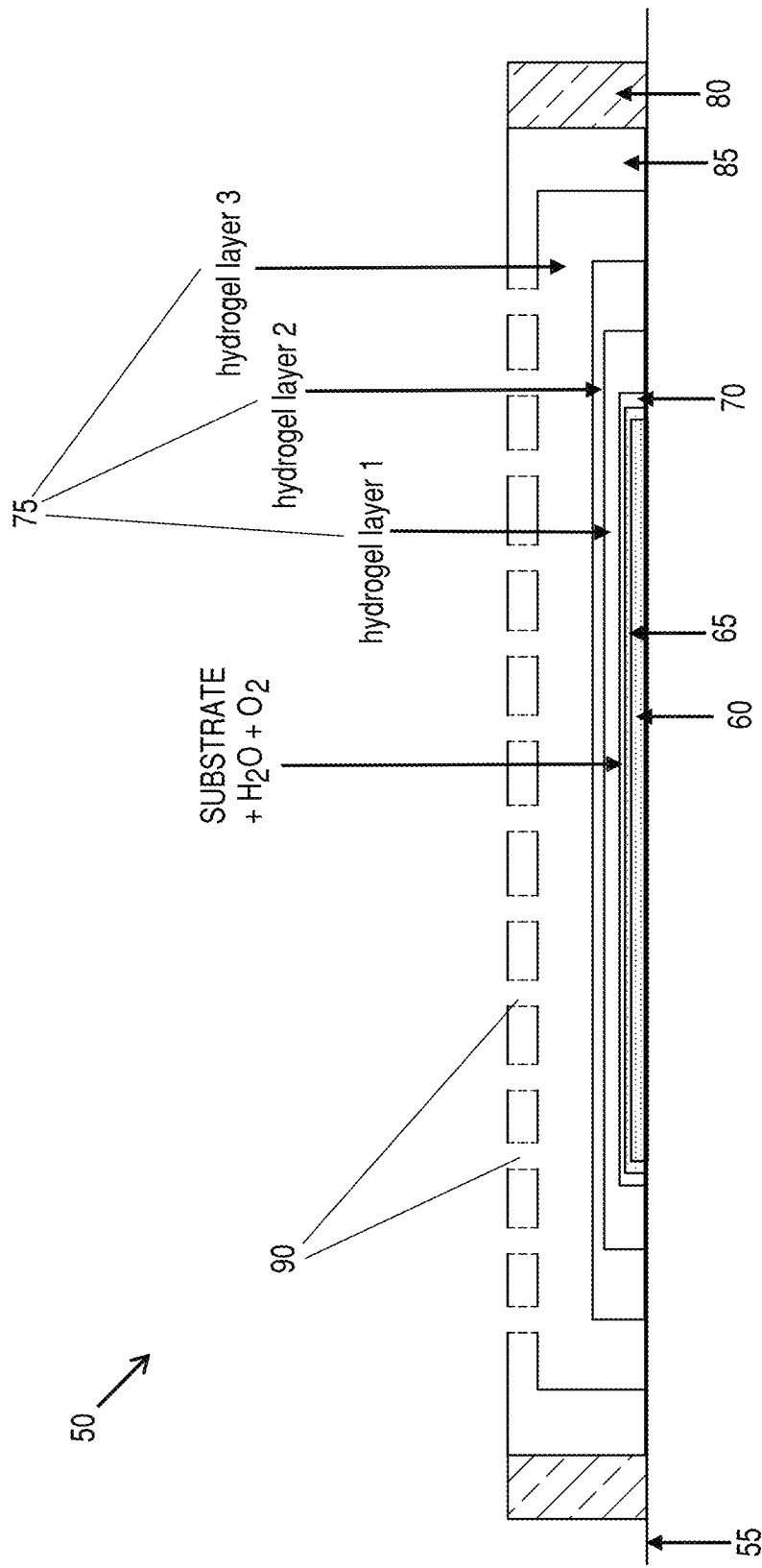
FIGS. 3 and 4 show processing steps and respective structures in accordance with some aspects of the present invention.

FIG. 3 shows a biosensor structure 50 comprising a wafer 55. In some embodiments, the wafer 55 may comprise a bulk silicon or silicon on insulator (SOI) wafer. More specifically, FIG. 3 shows an exemplary wafer 55 employed as an intermediate structure. The wafer 55 may be fabricated using techniques well known to those skilled in the art. For example, the wafer 55 may be thermally oxidized and may have a thickness of about 10 kÅ; however, the invention is not limited to these dimensions, and the various portions of the wafer 55 may have any desired thicknesses.

As shown in FIG. 3, the wafer 55 may comprise multiple areas upon which a working electrode 60 and a reference electrode may be built either simultaneously or at separate stages of manufacture. For example, the wafer 55 may comprise a working electrode 60 formed in a first area of the wafer and a reference electrode (not shown) formed in a second area of the wafer. However, the biosensor structure 50 is not limited to only one working electrode and one reference electrode. The working electrode 60 may be microfabricated as an array of connected microelectrodes, and the biosensor structure 50 may additionally comprise contact pads and wiring layers (e.g., a lead wire) that may be fabricated either simultaneously or at separate stages of manufacture as the working electrode and the reference electrode.

More specifically, the working electrode 60 may be formed comprising a metal layer 65 selectively formed over the wafer 55. Particularly, the metal layer 65 may be formed through electroplating by selective electrodeposition on a seed layer or sputtered (e.g., physical vapor deposition PVD) onto an adhesion layer. In accordance, the metal layer 65 may be selectively formed over the seed layer or adhesion layer using conventional materials and biosensor fabrication techniques, such as using a hard mask or a photoresist. In particular, a photoresist mask may be formed on the seed layer or adhesion layer such that the metal layer 65 is only electroplated or sputtered to the seed layer or adhesion layer in areas pertaining to electrodes, contact pads, and/or wiring (e.g., forming a working electrode in an area with a diameter in the range of 10 μm to 1000 μm). For example, the biosensor 50 and metal layer 65 may be patterned using standard contact lithographic techniques including Fusion systems hardening of a OIR906 photoresist. Reactive ion etching (ME) of the metal layer may be performed in a Tegal 6540 using chlorine.

In some embodiments, the metal layer 65 may be comprised of gold, silver, platinum, and/or iridium, and may have a thickness from 200-1,400 Å, e.g., from 500-900 Å, with a resistivity from 0.4-5.3 Ω/m. Additionally, the adhesion layer may be comprised of titanium-tungsten (TiW), and may have a thickness from 200-1,000 Å, e.g., from 200-400 Å, with a resistivity of from 25-32 Ω/m. However, the invention is not limited to these materials or dimensions, and the metal layer 65 may be comprised of any desired materials in any desired thicknesses.

In order to attenuate signals from electrochemical interferents and promote adhesion of subsequent hydrogel films, a permselective layer 70 (e.g., a silane layer) may be selectively patterned onto the wafer 55 (e.g., over the working electrode). As shown in FIG. 3, the permselective layer 70 may be formed by initially preparing an alcohol solution (e.g., 10 g of alcohol solution) of a silane compound, N-(2-aminoethyl)-3-aminopropyltrimethoxysilane or gamma amino silane, by mixing the silane compound (e.g., 2 mL), in water (e.g., 50 mL), and ethanol (50 mL) or 2-propanol (50 g). In accordance with some aspects of the invention, the alcohol solution may then be deposited (e.g., spin coated) over the wafer 55 to a predetermined thickness. The permselective layer 70 may have a thickness of about 80 Å; however, the invention is not limited to these dimensions, and the various portions of the permselective layer 70 may have any desired thicknesses.

The wafer 55 and the permselective layer 70 may then be heated (e.g., heated to about 160° C. for about 15 minutes) to dry and set the permselective layer 70. A photoresist (e.g., a positive photoresist (Shipley, S1813)) may then be deposited (e.g., spin coated) onto the wafer 55 and the permselective layer 70, soft-baked (e.g., baked at about 100° C. for about 60 seconds), and patterned (e.g., by means of exposure to ultraviolet light) through a mask. The resist may then be developed (e.g., Shipley, 455) to leave a resist cap over and around the working electrode 60 and a lead line (not shown). The exposed permselective layer 70 may then be selectively etched (e.g., plasma etched using oxygen and carbon tetrafluoride plasma for about 90 seconds). The remaining photoresist may then be stripped (e.g., using an acetone bath) followed by a rinsing (e.g., using a 2-propanol bath).

Optionally, the permselective layer 70 may be selectively wet etched rather than plasma etched. For example, following the patterning of the photo resist, the wafer 55 may be etched (e.g., etched in a 1/500 fold dilution of hydrofluoric acid (10 M) in deionized water) to remove portions of the permselective layer 70 (e.g., polymerized N-(2-aminoethyl)-3-aminopropyltrimethoxysilane) not protected by the photoresist. Other protic solvents, such as lower alkanols, may be used as the solvent for the hydrofluoric acid. Mixtures of protic solvents may also be used. Typically, the concentration of hydrofluoric acid in the protic solvent may be in the range of about 0.001 to about 0.01 weight percent. The resist cap may then be removed by exposure of the wafer 55 to n-butylacetate followed by ultrasonication (e.g., ultrasonication for 15 minutes). Thereafter, the wafer 55 may be baked dry (e.g., baked at about 100° C. for about 60 minutes).

In alternative embodiments, the permselective layer 70 (e.g., the silane layer) may be fabricated using a "lift-off" process where the photoresist is first patterned and the permselective layer 70 is coated over the photoresist. For example, a layer of photoresist (e.g., positive photoresist (Shipley, S1813)) may be deposited (e.g., spin-coated) over the wafer 55 and baked to dry (e.g., soft-baked at about 90° C. for about 30 minutes). The photoresist may then be patterned as described previously to leave the area over the working electrode exposed. An alcohol solution of the permselective layer 70 (e.g., 0.5 g/dL solution of N-(2-aminoethyl)-3-aminopropyltrimethoxysilane in deionized water) may then be deposited (e.g., spin coated) onto the wafer 55 and baked to dry (e.g., baked at about 90° C. to 250° C. for about 5 to 30 minutes) under an inert atmosphere. Excess permselective layer 70 (e.g., polymerized silane) and photoresist may then be removed (e.g., by means of ultrasonication in n-butylacetate for about 15 minutes). After the photoresist is removed, the wafer 55 may be baked to dry (e.g., baked at about 160° C. for about 15 minutes).

These fabrication processes should provide an intermediate biosensor structure 50 comprising a wafer 55 in which the permselective layer 70 is localized over the working electrode, as shown in FIG. 3.

In accordance with some aspects of the invention, additional photoformable hydrogel layers or biolayers 75 comprising one or more enzymes may be established on the intermediate biosensor structure 50 shown in FIG. 3 to sensitize the working electrode 60 specifically to an analyte of interest. In various embodiments of the present invention, the biolayers 75 may be formed by either spin coating or by microdispensing each layer (as discussed in detail below). More specifically, an aqueous enzyme-hydrogel matrix comprising one or more proteins and a photoformable hydrogel such as styrylpyridinium polyvinylalcohol (SBQ-PVA) supplied by Charkit Chemical Corp., Norwalk, Conn. may be utilized for immobilizing enzymes on or near the working electrode 60. A sugar or sugar alcohol, such as sucrose, sorbitol, or mannitol, may also be included in the formulation to alter the porosity of the photoformed matrix and to help stabilize the enzymes. In accordance with some aspects of the invention, the one or more proteins may comprise SOX, CRH, CNH, catalase, lactate oxidase (LOX), glucose oxidase (GOX), and/or bovine serum albumin (BSA) mixed to obtain the enzymatic activities, water uptake and diffusional properties desired in each biolayer.

In addition to SBQ-PVA, other photo-crosslinkable materials, such as, epoxies, acrylamides acrylates and other vinyls given that the combination of protein, crosslinking agent, photoinitiator, and other additives may be found to have suitable negative photoresist characteristics may be used in accordance with some aspects of the present invention. For example, the hydrogel layers may further comprise a matrix comprising PVA, gelatin, acrylamide, polyethyleneglycol diacrylate, or combinations thereof.

In embodiments comprising spin coating, the biolayers 75 layers may be photolithographically patterned using ultraviolet light to crosslink the material using a mask followed by removal of the non-crosslinked material such that the biosensor structure 55 is selectively coated. In embodiments comprising microdispensing, an appropriate quantity of each coating may be applied to an area circumscribed by an additional structural component (e.g., optional additional structure 80) configured as a containment device. In accordance with some aspects of the invention, the biolayers 75 may be formed such that a diameter of each successive biolayer increases over that of the diameter of the working electrode.

In some embodiments, an additional attenuation layer 85 (e.g., a photo definable layer comprising methyl-silicone polycarbonate (MSP) hydrophobic polymer (Dow WL7154)) may be spin coated or printed over the biolayers 80 (e.g., the SBQ-PVA/BSA layer) to further attenuate the analyte from reaching the detection biolayer, while at the same time allowing oxygen to be in stoichiometric excess. The additional attenuation layer 85 may be exposed to ultraviolet light through an appropriate mask, and unexposed portions can be developed using a developer such as 1,3,5 trimethylbenzene. Vias 90 may be formed through the additional attenuation layer 85 using conventional biosensor fabrication techniques, such as etching the additional attenuation layer 85 through a mask, which may be a hard mask or a photoresist. The vias 90 may be configured such that the sample comes into contact with the photoformable hydrogel layer 80 allowing the analyte to diffuse to the photoformable hydrogel layer 80 in a controlled and reproducible manner.

As should be understood, the methods described above may be used in the fabrication of biosensor chips. The resulting biosensor chips can be distributed by the fabricator in raw wafer form (that is, as a single wafer that has multiple unpackaged chips), as a bare die, or in a packaged form. In the latter case biosensor chips may be mounted in a single chip package (such as a plastic carrier, with leads that are affixed to a circuit board or other higher level carrier) or in a multichip package (such as a ceramic carrier that has either or both surface interconnections or buried interconnections). In any case, the biosensor chips may then be integrated with other chips, discrete circuit elements, and/or other signal processing devices as part of either (a) an intermediate product, such as a circuit board, or (b) an end product. The end product can be any product that includes the biosensor chips such as a cartridge that is designed to deliver fluid to the sensor and isolate the electronics from the fluid.

Biolayer Fabrication Using Spin Coating

The descriptions of various embodiments of the present invention are presented hereafter for purposes of illustration, but are not intended to be exhaustive or limited to the embodiments disclosed. Many modifications and variations of the various biolayers should be apparent to those of ordinary skill in the art without departing from the scope and spirit of the described embodiments.

Figure 4:
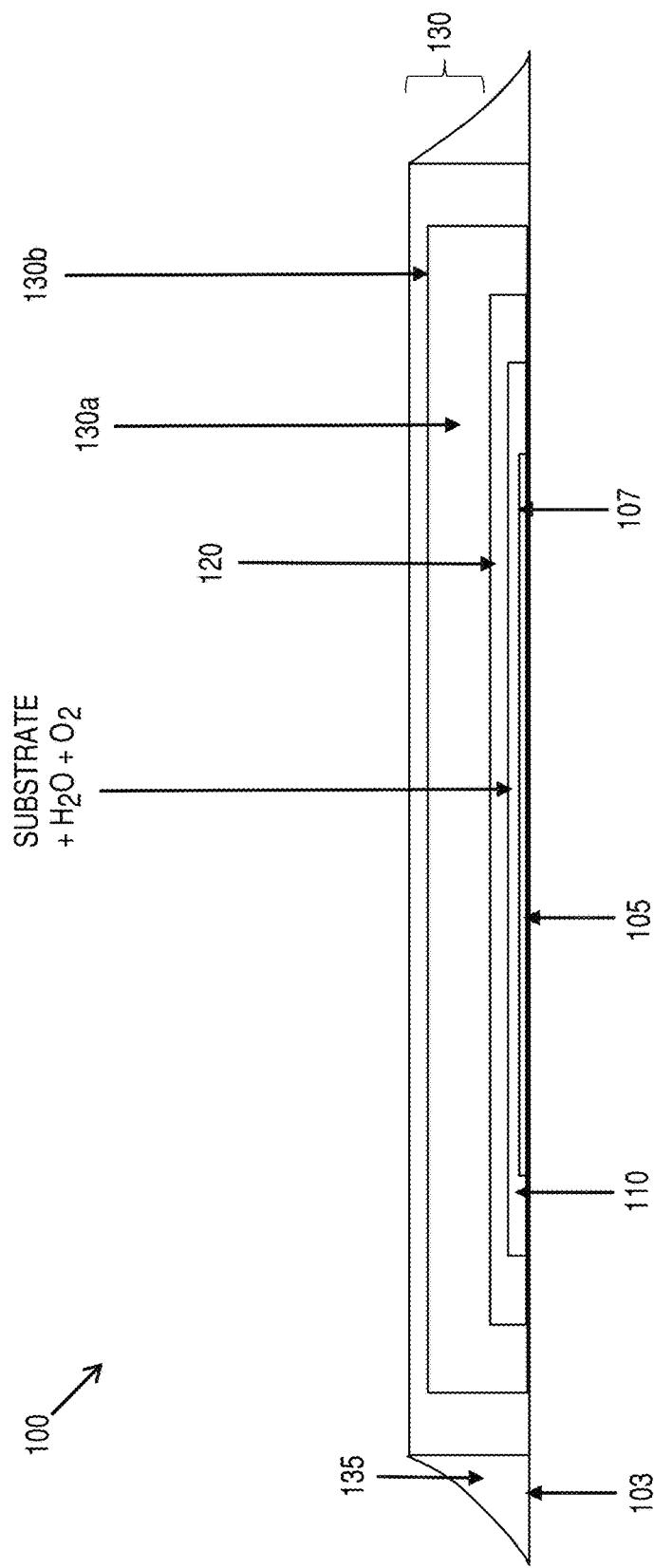

FIG. 4 shows a creatinine biosensor 100 fabricated in accordance with some aspects of the present invention. For example, the biosensor 100 may comprises a base biosensor structure (e.g., wafer 103, working electrode 105, and silane layer 107 fabricated as described above with respect to FIG. 3) and three biolayers (110, 120, and 130) fabricated using a spin-coated process as described in further detail below. More specifically, biolayer 130 may be configured as two screening biolayers 130a and 130b each comprising CRH, SOX and Catalase such that creatine may be selectively screened from a sample. In accordance with some aspects of the invention, the two screening biolayers 130a and 130b may be formed in two separate spin-coating steps. Biolayer 120 may be configured as a diffusion biolayer comprising CRH such that the two screening biolayers 130a and 130b are separated from the creatinine detection biolayer 110. Creatinine detection biolayer 110 may comprise CNH, CRH, and SOX such that the creatinine may be reduced to detectable hydrogen peroxide in the presence of a substrate that is free to diffuse through the multiple biolayers.

More specifically, biolayer 110 may be formed as an enzyme-hydrogel matrix including CNH, CRH, SOX, SBQ-PVA, and sucrose in various concentrations (e.g., about 1% CNH, about 4% CRH, about 1% SOX, about 4% sucrose, and about 11% SBQ-PVA (wherein all % are in w/w), a predetermined viscosity (e.g., a viscosity in the range of 1.0 to 1.5 Pascal-second), a water content of about 80 to 95 weight-percent, and a solid content of about 5 to 20 weight-percent. The biolayer 110 may be spun (e.g., at a speed in a range of 1000 to 2000 rpm) onto the wafer 103 and the working electrode 105. For example, biolayer 110 may be spun onto the wafer 103 and working electrode 105 by dispensing about 6 mL of solution onto the center of the wafer 103 and spinning at about 1200 rpm for 4 seconds and then at about 1850 rpm for 15 seconds. In one embodiment, the spin-coat process should form a biolayer with a thickness of about 1-5 μm, preferably 2-5 μm. The biolayer may then be substantially dried or cured to remove water content of the biolayer below a threshold value. For example, the drying of the biolayer may reduce the water content of the biolayer below a threshold value of about 2 weight-percent. After curing, the biosensor structure may be exposed to ultraviolet light (e.g., about 6 mW/cm$^2$, for about 10-30 seconds) to crosslink the polymer (e.g., SBQ-PVA) through an appropriate mask and developed using water to wash away the non-crosslinked polymer.

Biolayer 120 may be formed as an enzyme-hydrogel matrix including CRH, SBQ-PVA, and sucrose in various concentrations (e.g., about 6% CRH, about 4% sucrose, and about 9% SBQ-PVA (wherein all % are in w/w), a predetermined viscosity (e.g., a viscosity in the range of 1.0 to 1.5 Pascal-second), a water content of about 80 to 95 weight-percent, and a solid content of about 5 to 20 weight-percent. The biolayer 120 may be spun onto the wafer 103 and the biolayer 110 as described above. For example, biolayer 120 may be spun onto the wafer 103 and the biolayer 110 by dispensing about 6 mL of solution onto the center of the wafer 103 and spinning at about 1200 rpm for 4 seconds and then at about 1850 rpm for 15 seconds. In one embodiment, the spin-coat process should form a biolayer with a thickness of about 1-5 μm, preferably 2-5 μm. After curing as described above, the biosensor structure may be exposed to ultraviolet light (e.g., about 6 mW/cm$^2$, for about 10-30 seconds) through an appropriate mask. In some embodiments, the biolayer 120 is selectively exposed to UV light to crosslink the polymer (e.g., SBQ-PVA) but not subsequently developed. Instead, biolayer 120 may be left on the wafer in an undeveloped state.

Biolayer 130a may be formed as an enzyme-hydrogel matrix including CRH, SOX, SBQ-PVA, catalase and sucrose in various concentrations (e.g., about 5% CRH, about 1% SOX, about 4% sucrose, and about 10% SBQ-PVA (wherein all % are in w/w), a predetermined viscosity (e.g., a viscosity in the range of 1.0 to 1.5 Pascal-second), a water content of about 80 to 90 weight-percent, and a solid content of about 5 to 20 weight-percent. The biolayer 130a may be spun onto the wafer 103 and the biolayer 120 as described above. For example, biolayer 130a may be spun onto the wafer 103 and the biolayer 120 by dispensing about 6 mL of solution onto the center of the wafer 103 and spinning at about 1200 rpm for 4 seconds and then at about 1850 rpm for 15 seconds. In one embodiment, due to the fact that biolayer 120 was not developed and left present across all of the wafer 103, a thicker biolayer (e.g., a biolayer with a thickness of about 8-20 μm, preferably 8-10 μm) may be produced. After curing as described above, the biosensor structure may be exposed to ultraviolet light (e.g., about 6 mW/cm$^2$, for about 10-30 seconds) through an appropriate mask and developed to crosslink the polymer (e.g., SBQ-PVA). Water may then be used to wash away the non-crosslinked polymer.

Biolayer 130b may be formed as an enzyme-hydrogel matrix including CRH, SOX, SBQ-PVA, catalase and sucrose in various concentrations (e.g., about 5% CRH, about 1% SOX, about 4% sucrose, and about 10% SBQ-PVA (wherein all % are in w/w), a predetermined viscosity (e.g., a viscosity in the range of 1.0 to 1.5 Pascal-second), a water content of about 80 to 95 weight-percent, and a solid content of about 5 to 20 weight-percent. The biolayer 130b may be spun onto the wafer 103 and the biolayer 130a as described above. For example, biolayer 130b may be spun onto the wafer 103 and the biolayer 130a by dispensing about 6 mL of solution onto the center of the wafer 103 and spinning at about 1200 rpm for 4 seconds and then at about 1850 rpm for 15 seconds. In one embodiment, the spin-coat process should form a biolayer with a thickness of about 1-5 μm. After curing as described above, the biosensor structure may be exposed to ultraviolet light (e.g., about 6 mW/cm$^2$, for about 10-30 seconds) to crosslink the polymer (e.g., SBQ-PVA) through an appropriate mask and developed using water to wash away the non-crosslinked polymer.

As should be understood, biolayer 103b may be firmly anchored to the wafer 103 and feature 135 serves to round the contour of the biosensor structure because biolayer 130b has a larger surface area than the underlying biolayers. Advantageously, this may allow the biolayers to be robustly held in place in order to withstand any forces associated with a wet saw dicing process, which may be used to singulate the wafer into individual biosensors.

In accordance with above-described processes, biolayer 110 may be configured as a creatinine detection layer and produces hydrogen peroxide when creatinine is present in the sample. Biolayer 120 may be configured to separate the detection layer from the screening layers and provides additional CRH enzyme for both detection and screening purposes. In addition, during the spin coating process biolayer 120 assists in increasing the thickness of the third enzyme layer because biolayer 120 is not developed and acts as a sponge as discussed in detail below. Biolayer 130a may be configured to remove creatine from the sample before the creatine can reach biolayer 110 where the creatine may interfere with the detection of creatinine. Biolayer 130b may also help to eliminate creatine interference and may serve as a cap to anchor the biolayers to the wafer 103.

A should be understood by those of ordinary skill in the art, the above-described process provide a modified spin coating process that may be used to create at least one biolayer thicker (e.g., a layer thickness of >5-12 μm) than achieved with typical spin coating processes. The modification comprises leaving an underlying hydrogel layer undeveloped prior to applying a new hydrogel layer. Therefore, the underlying hydrogel acts as a sponge soaking up water from the new hydrogel layer since the underlying hydrogel has not been developed, which dehydrates or dries the new hydrogel layer as the new hydrogel layer spreads across the biosensor structure. This enhanced drying effect causes a uniform thicker biolayer to be produced. Although the new biolayer may be thicker after exposure, the new biolayer and the underlying biolayer can be developed thereafter as described above. Advantageously, the spin coating processes described herein overcomes layer thickness limitations associated with traditional spin coating enzyme-biolayer matrixes onto a substrate.

Figure 5:
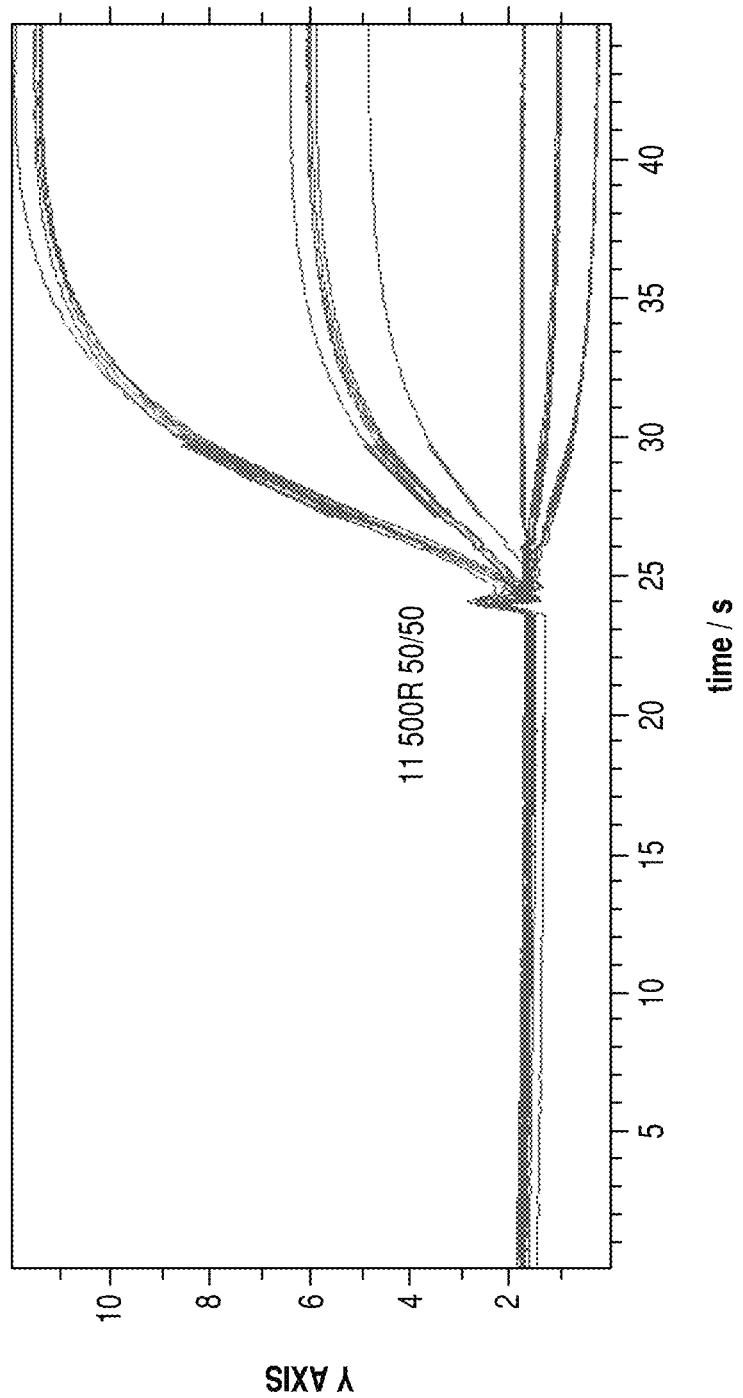
FIGS. 5 and 6 show creatinine related test data in accordance with some aspects of the invention.
Figure 6:
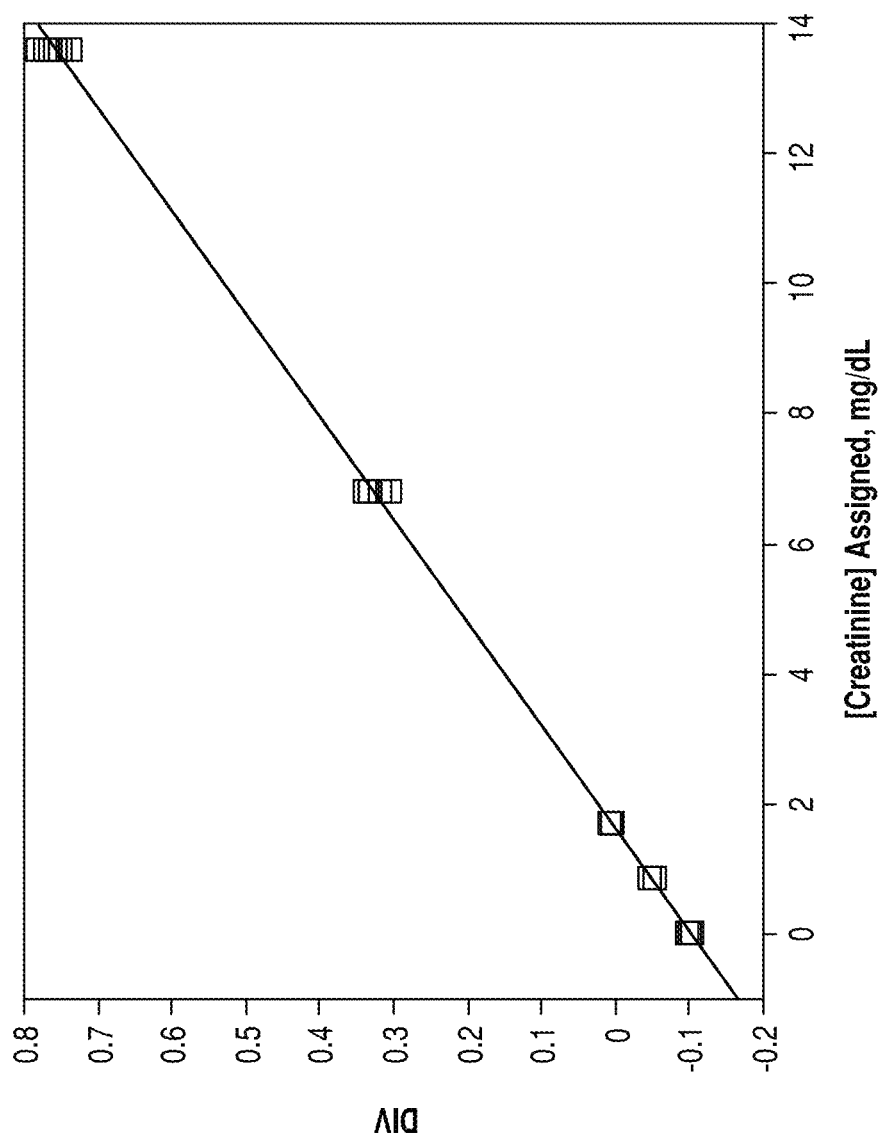

FIG. 5 shows a response, in nanoamps of the creatinine biosensor 100 to samples with various levels of creatinine (e.g., 0, 1, 2, 6.8, and 13.6 mg/dL). During the first 23 seconds, a calibrant solution is in contact with the creatinine biosensor 100, which is followed by the sample. The calibrant response (17-20 seconds) is taken just before the samples are put in front of the creatinine biosensor 100 and the sample signals are taken at a time when the sample response is at its steepest (27-30 seconds). The sensor response may be normalized by dividing the slope of the sample response by the corresponding calibrant response of the sensor (DIV). FIG. 6 shows a plot of the DIV response for the various concentration of creatinine samples tested. The linearity of the response over this range shows a considerable improvement for creatinine detection using the creatinine biosensor 100 over traditional creatinine biosensors.

Figure 7:
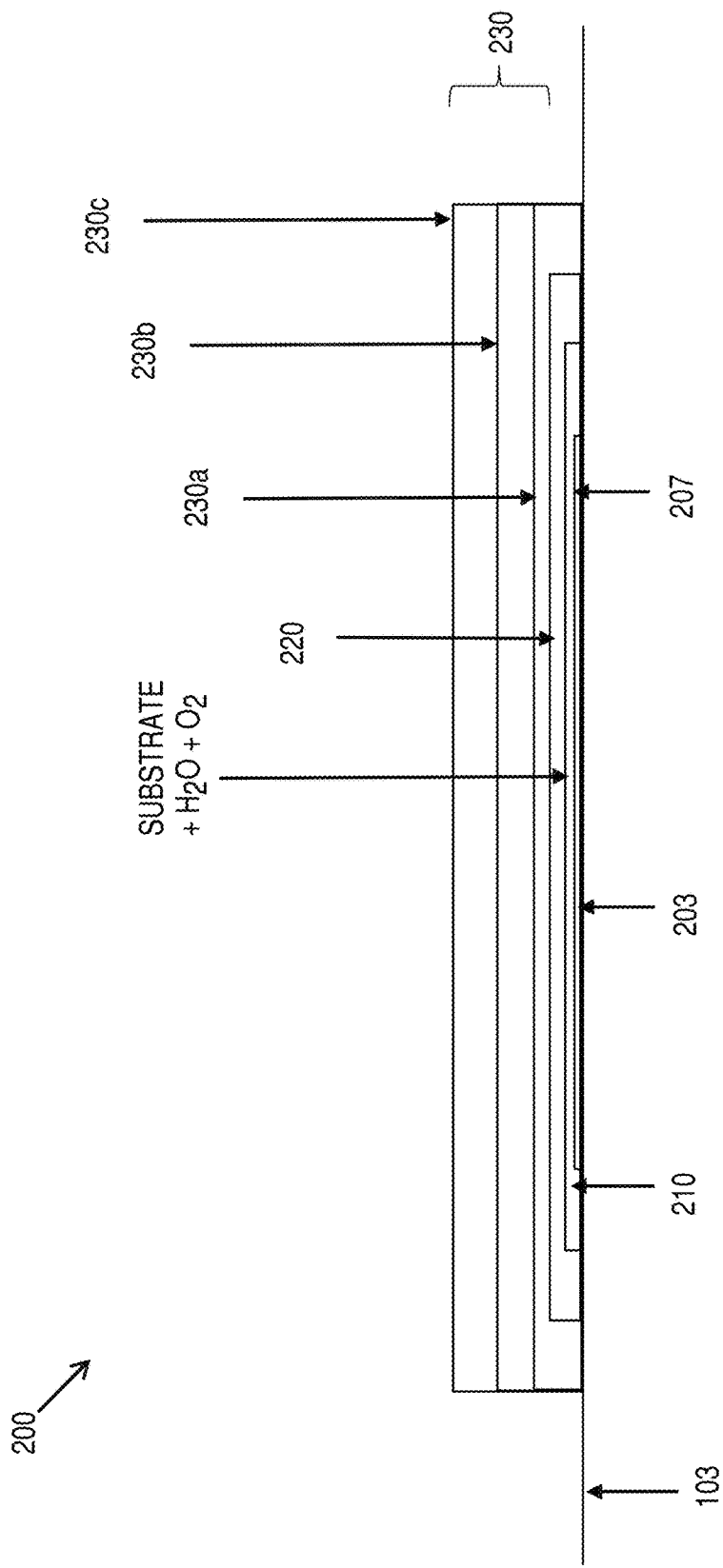
FIGS. 7 and 8 show processing steps and respective structures in accordance with some aspects of the present invention.

FIG. 7 shows a creatinine biosensor 200 fabricated using an alternative spin coating process in accordance with some aspects of the present invention. For example, the biosensor 200 comprises a base biosensor structure (e.g., wafer 203, working electrode 205, and silane layer 207 fabricated as described above with respect to FIG. 3) and three biolayers (210, 220, and 230) fabricated using a spin-coated process. More specifically, biolayer 230 may be configured as three screening biolayers 230a, 230b, and 230c each comprising CRH and SOX such that creatine may be selectively screened from a sample. In accordance with some aspects of the invention, the three screening biolayers 230a, 230b, and 230c may be formed in two or three separate spin-coating steps. Biolayer 220 may be configured as a diffusion biolayer comprising CRH such that the three screening biolayers 230a, 230b, and 230c are separated from the creatinine detection biolayer 210. Creatinine detection biolayer 210 may comprise CNH, CRH, and SOX such that creatinine may be reduced to detectable hydrogen peroxide in the presence of a substrate that is free to diffuse through the multiple biolayers.

More specifically, biolayer 210 may be formed as an enzyme-hydrogel matrix as discussed-above with respect to biolayer 110 in FIG. 4. Biolayer 220 may be formed as an enzyme-hydrogel matrix as discussed-above with respect to biolayer 120 in FIG. 4 except that the biolayer 220 is UV exposed to crosslink the polymer (e.g., SBQ-PVA) and subsequently developed using water to remove the non-crosslinked polymer. Biolayer 230*a* may be formed as an enzyme-hydrogel matrix as discussed-above with respect to biolayer 130*a* in FIG. 4 except that since biolayer 220 was developed, biolayer 230*a* may be formed as a thinner layer (e.g., a biolayer with a thickness of about 1-5 µm). Additionally, biolayer 230*a* after crosslinking the polymer (e.g., SBQ-PVA) may not be subsequently developed using water to remove the non-crosslinked polymer, but may instead be left on the biosensor structure in an undeveloped state. Biolayer 230*b* may be formed as an enzyme-hydrogel matrix as discussed-above with respect to biolayer 130*b* in FIG. 4; however, due to the fact that biolayer 230*a* was not developed and left present across all of the wafer 203 a thicker layer (e.g., a biolayer with a thickness of about 8-20, preferably 8-10 µm) may be produced. Additionally, biolayer 230*b* may not be subsequently developed using water to remove the non-crosslinked polymer, but may instead be left on the biosensor structure in an undeveloped state. Biolayer 230*c* may be formed as an enzyme-hydrogel matrix as discussed-above with respect to biolayer 130*b* in FIG. 4; however, due to the fact that biolayer 230*b* was not developed and left present across all of the wafer 203 a thicker layer (e.g., a biolayer with a thickness of about 8-20, preferably 8-10 µm) may be produced. Additionally, biolayer 230*c* may be exposed to ultraviolet light to crosslink the polymer (e.g., SBQ-PVA) and subsequently developed using water to remove the non-crosslinked polymer. Advantageously, the additional thick screening biolayer (e.g., biolayer 230*c* at about 8-20, preferably 8-10 µm) improves the creatine removal before the creatine reaches the detection biolayer 210.

Biolayer Fabrication Using Microdispensing

The descriptions of various embodiments of the present invention are presented hereafter for purposes of illustration, but are not intended to be exhaustive or limited to the embodiments disclosed. Many modifications and variations of the various biolayers should be apparent to those of ordinary skill in the art without departing from the scope and spirit of the described embodiments.

Figure 8:
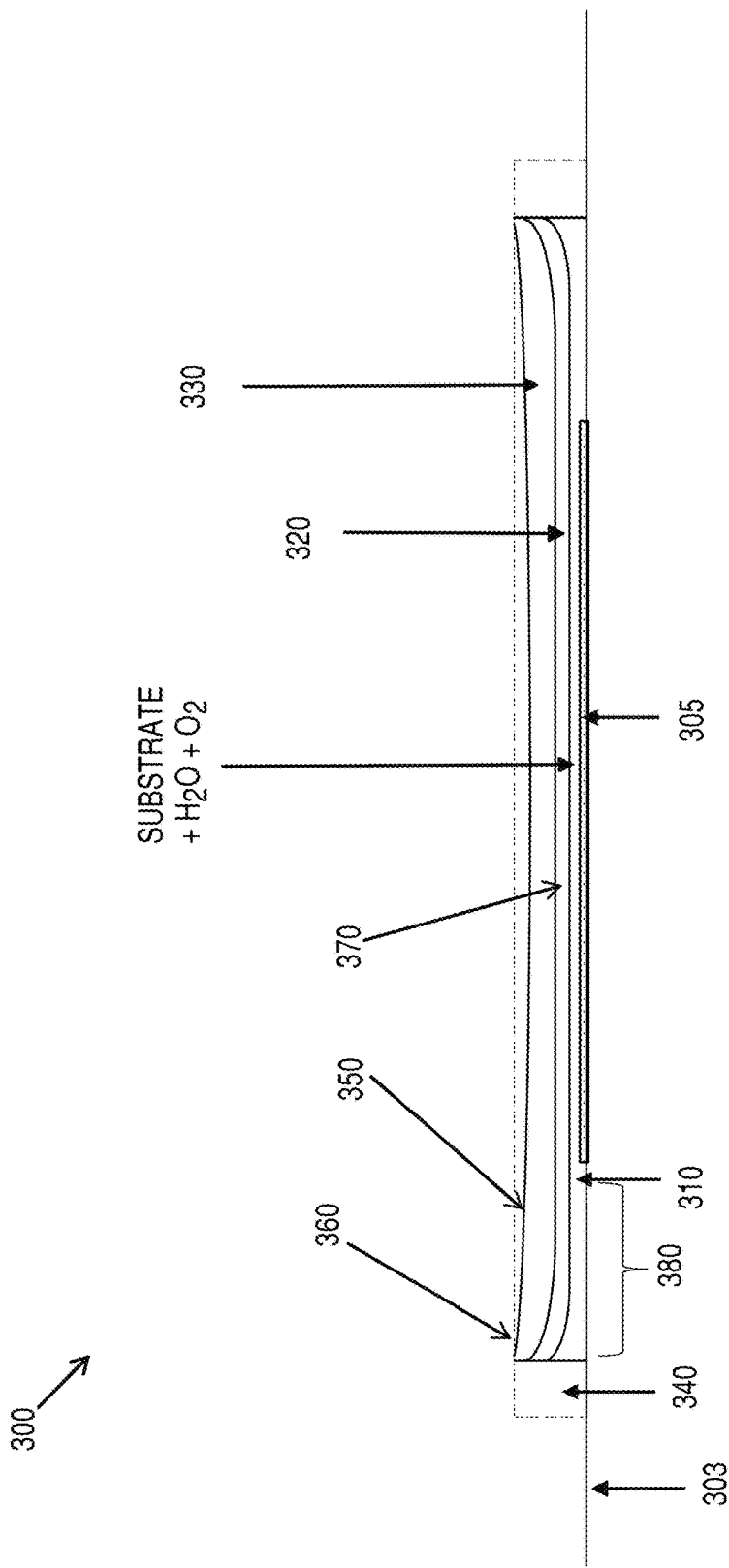

FIG. 8 shows a creatinine biosensor 300 fabricated in accordance with some aspects of the present invention. For example, the biosensor 300 may comprise a base biosensor structure (e.g., wafer 303 and working electrode 305 fabricated as described above with respect to FIG. 3) and three biolayers (310, 320, and 330) fabricated using a microdispensing or printing process as described in further detail below. More specifically, biolayer 330 may be configured as a screening biolayer comprising CRH, SOX and catalase such that creatine may be selectively screened from a sample. Biolayer 320 may be configured as a diffusion biolayer comprising CRH such that the screening biolayer is separated from the creatinine detection biolayer 310. Creatinine detection biolayer 310 may comprise CNH, CRH, and SOX such that the creatinine may be reduced to detectable hydrogen peroxide in the presence of a substrate that is free to diffuse through the multiple biolayers.

More specifically, biolayer 310 may be formed as an enzyme-hydrogel matrix including CNH, CRH, SOX, SBQ-PVA, and sucrose in various concentrations (e.g., about 0.4% CNH, about 1.5% CRH, about 0.2% SOX, about 1% sucrose, and about 3% SBQ-PVA (wherein all % are in w/w) and a predetermined viscosity (e.g., about 0.3 P (0.12 N s $m^{-2}$)). The biolayer 310 may be dispensed onto the wafer 303 and the working electrode 305 as described above. For example, the biolayer 310 may be dispensed onto the wafer 303 by use of partial drop transfer of solution onto the working electrode 305 to fill a formed additional structure or containment ring 340 (e.g., about 1 nL). The biolayer may then be substantially dried or cured to remove water content of the biolayer below a threshold value. For example, the drying of the biolayer may reduce the water content of the biolayer below a threshold value of about 2 weight-percent. After drying, the biolayer 310 may be exposed to ultraviolet light (e.g., about 6 mW/cm$^2$, for 10-30 seconds) to crosslink the polymer (e.g., SBQ-PVA) and developed. In some embodiments, the drying of the biolayer 310 may be performed in low relative humidity (e.g., about 5-20% RH). The low relative humidity may result in a cross sectional profile 350 of the biolayer 310 that may not be planar (e.g., a substantially concave shape). Instead, the biolayer 310 has a thick ring 360 around the edge. However, the biolayer 310 is of uniform thickness 370 over the working electrode 305 because the extension 380 is configured to absorb the thick ring 360 non-planar profile 350.

Biolayer 320 may be formed as an enzyme-hydrogel matrix including CRH, SBQ-PVA, and sucrose in various concentrations (e.g., about 1.4% CRH, about 1% sucrose, and about 3% SBQ-PVA (wherein all % are in w/w) and a predetermined viscosity (e.g., about 0.4 P (0.13 N s $m^{-2}$)). The biolayer 320 may be dispensed onto the wafer 303 and the biolayer 310 as described above. For example, the biolayer 320 may be dispensed onto the wafer 303 by use of partial drop transfer of solution onto the working electrode 305 in sufficient volume to completely cover biolayer 310 (e.g., about 1 nL). After drying as described above, the biolayer 320 may be exposed to ultraviolet light (e.g., about 6 mW/cm$^2$, for 10-30 seconds) to crosslink the polymer (e.g., SBQ-PVA) and developed. In some embodiments, the underlying biolayer 310 may be configured to absorb water when the biolayer 320 is dispensed. Thus, biolayer 320 dries more quickly and evenly, and the cross sectional profile of the biolayer 320 is more planar than the biolayer 310 even though the same drying conditions are employed (e.g., about 5-20% RH).

Biolayer 330 may be formed as an enzyme-hydrogel matrix including CRH, SOX, SBQ-PVA, catalase and sucrose in various concentrations (e.g., about 2.5% CRH, about 0.4% SOX, about 0.4% catalase, about 0.6% sucrose, and about 5.3% SBQ-PVA (wherein all % are in w/w) and a predetermined viscosity (e.g., about 0.6 P (0.12 N s $m^{-2}$)). The biolayer 330 may be dispensed onto the wafer 303 and the biolayer 320 as described above. For example, the biolayer 330 may be dispensed onto the wafer 303 by use of partial drop transfer of solution onto the biolayer 320 in sufficient volume to completely cover biolayer 320 (e.g., about 1 nL). After allowing this layer to partially dry a second dispense may be performed, which doubles the thickness of the biolayer 330. In some embodiments, underlying biolayer 320 absorbs water when the biolayer 330 is dispensed. Thus, biolayer 330 dries more quickly and evenly, and the cross sectional profile of the biolayer 330 is even more planar than the biolayer 310 or the biolayer 320 even though the same drying conditions are employed (e.g., e.g., about 5-20% RH). After drying as described above, the biolayer 330 may be exposed to ultraviolet light (e.g., about 6 mW/cm$^2$, for 10-30 seconds) to crosslink the polymer (e.g., SBQ-PVA) and developed.

In accordance with the above-described processes, biolayer 310 may be configured as a creatinine detection layer and produces hydrogen peroxide when creatinine is present in the sample. Biolayer 320 may be configured to separate the detection layer from the screening layers and provides additional CRH enzyme for both detection and screening purposes. Biolayer 330 may be configured to remove creatine of the sample before the creatine can reach biolayer 310 where the creatine may interfere with the detection of creatinine.

A should be understood by those of ordinary skill in the art, the above-described microdispensing process may be used to advantageously create at least one biolayer in a controlled and cost efficient fashion as compared to typical spin coating processes. Advantageously, the drop dispensing wastes very little if any enzyme-hydrogel matrix.

Figure 9:
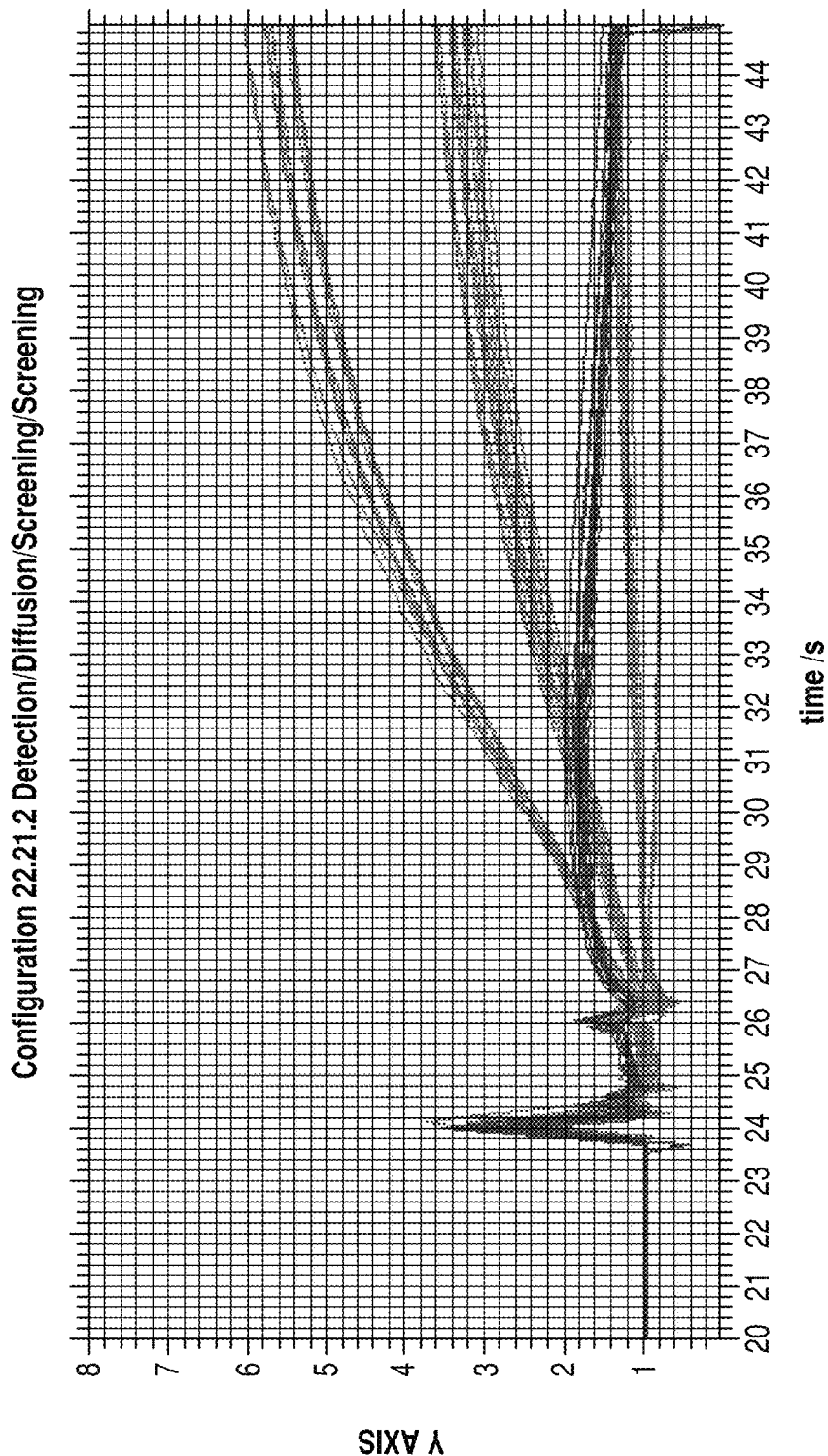
FIGS. 9-12 show creatinine related test data in accordance with some aspects of the invention.
Figure 10:
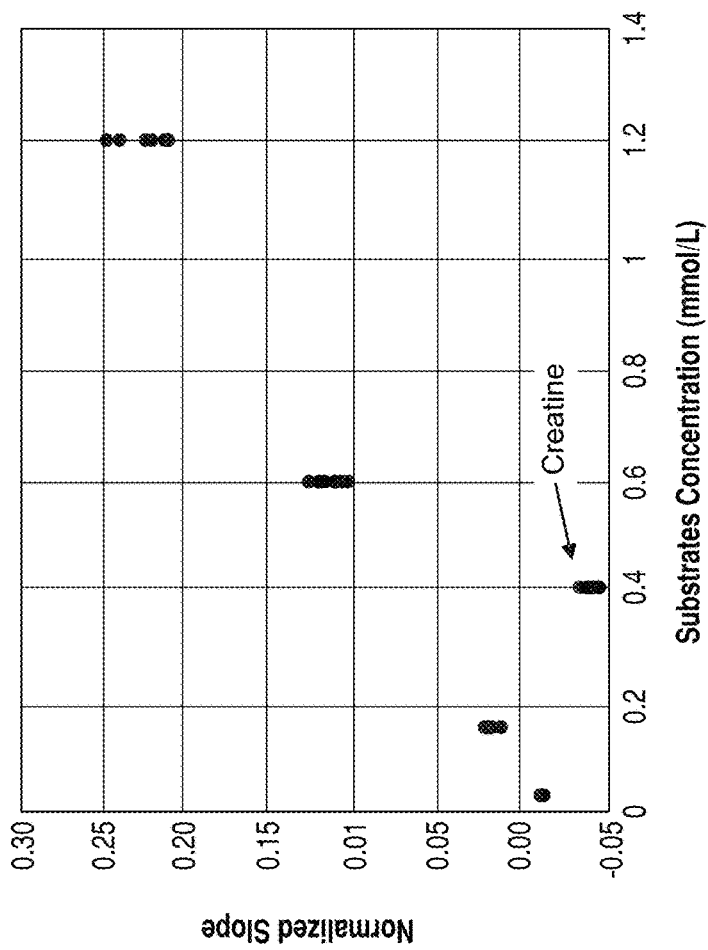

FIG. 9 shows a response, in nanoamps of the creatinine biosensor 300 to samples with various levels of creatinine (e.g., 0, 0.15, 0.6, 1.2 mmol/L). During the first 23 seconds, a calibrant solution is in contact with the creatinine biosensor 300, which is followed by the samples. The calibrant response (17-20 seconds) is taken just before the samples are put in front of the creatinine biosensor 300 and the sample signals are taken when the sample response is most stable (34-39 seconds). The sensor response may be normalized by dividing the slope of the sample response by the corresponding calibrant response of the sensor (DIV). FIG. 10 shows a plot of the DIV response for the various concentration of creatinine samples tested. The linearity of the response over this range shows a considerable improvement for creatinine detection using the creatinine biosensor 300 over traditional creatinine biosensors.

Figure 11:
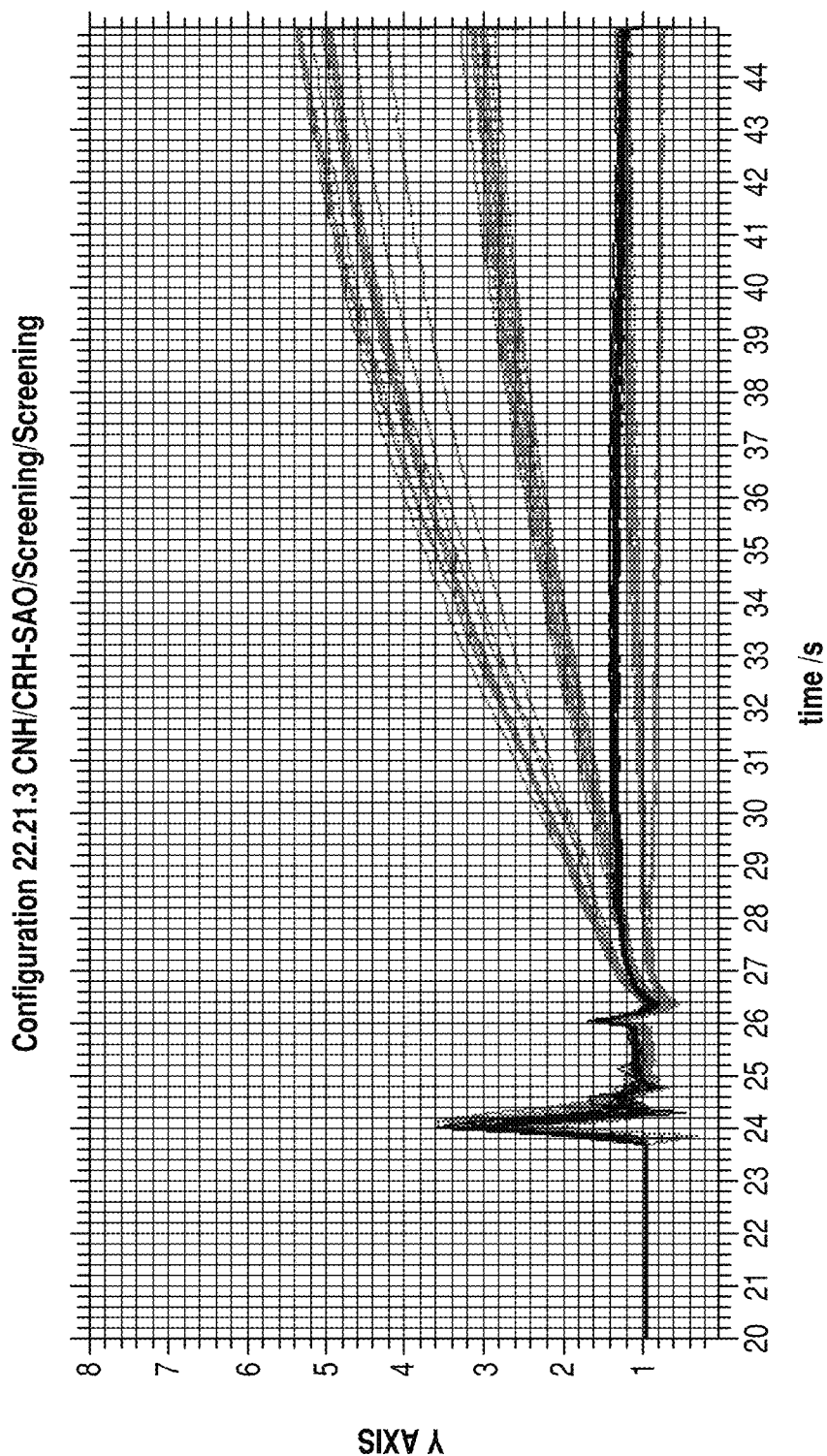
Figure 12:
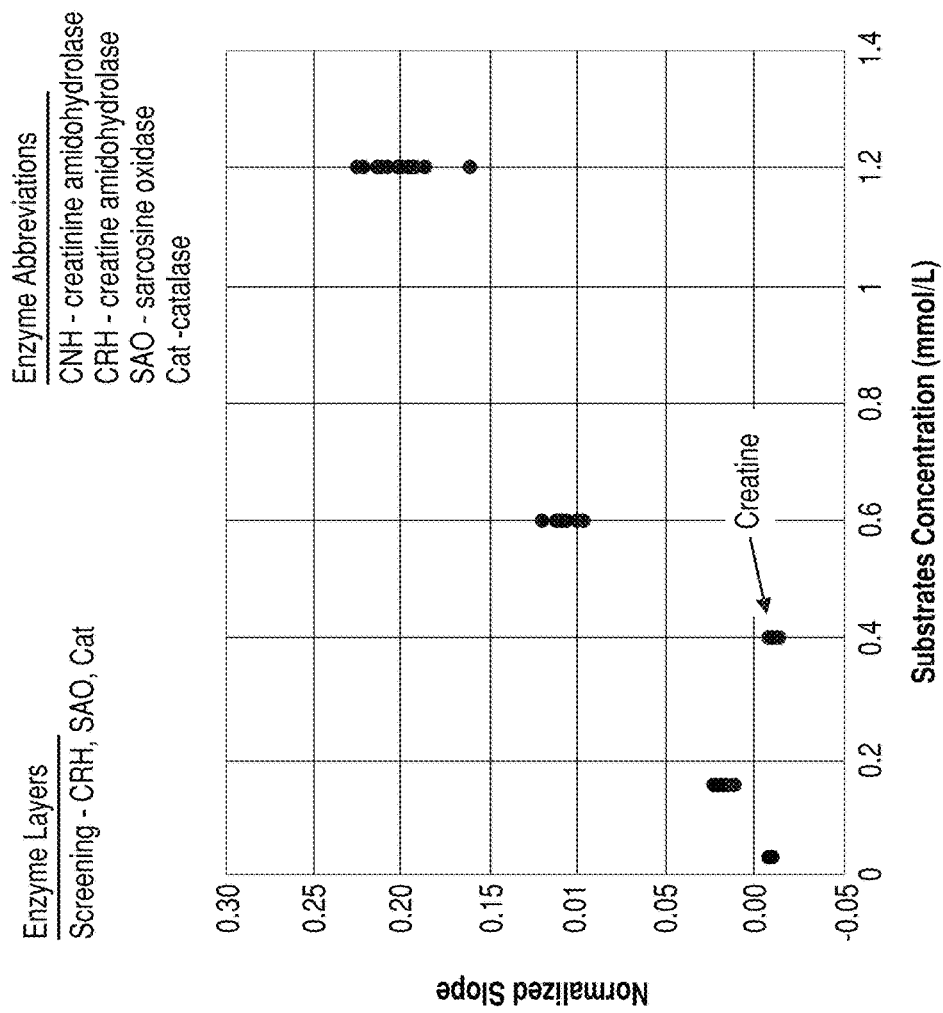

In alternative embodiments, the creatinine biosensor 300 may be modified such that biolayer 310 is configured as a detection biolayer comprising CNH such that creatinine is reduced to creatine, and detection biolayer 320 comprises CRH, and SOX such that the creatine may be reduced to detectable hydrogen peroxide in the presence of a substrate that is free to diffuse through the three biolayers. FIG. 11 shows a response, in nanoamps of this alternative creatinine biosensor 300 to samples with various levels of creatinine (e.g., 0, 0.15, 0.6, 1.2 mmol/L). During the first 23 seconds, a calibrant solution is in contact with the creatinine biosensor 300, which is followed by the sample. The calibrant response (17-20 seconds) is taken just before the samples are put in front of the creatinine biosensor 300 and the sample signals are taken when the sample kinetic response is most stable (32-39 seconds). The sensor response may be normalized by dividing the slope of the sample response by the corresponding calibrant response of the sensor (DIV). FIG. 12 shows a plot of the DIV response for the various concentration of creatinine samples tested. This plot shows improved chemical removal of creatine interference and a reduced flux of creatine to the detection layer. Therefore, a lower detection signal (i.e., reduction of a positive interferent), however the loss of negative slope response for creatine may be achieved thereby appearing to give less creatine discrimination when using the slope of the sample signal as the analytical response.

Figure 13:
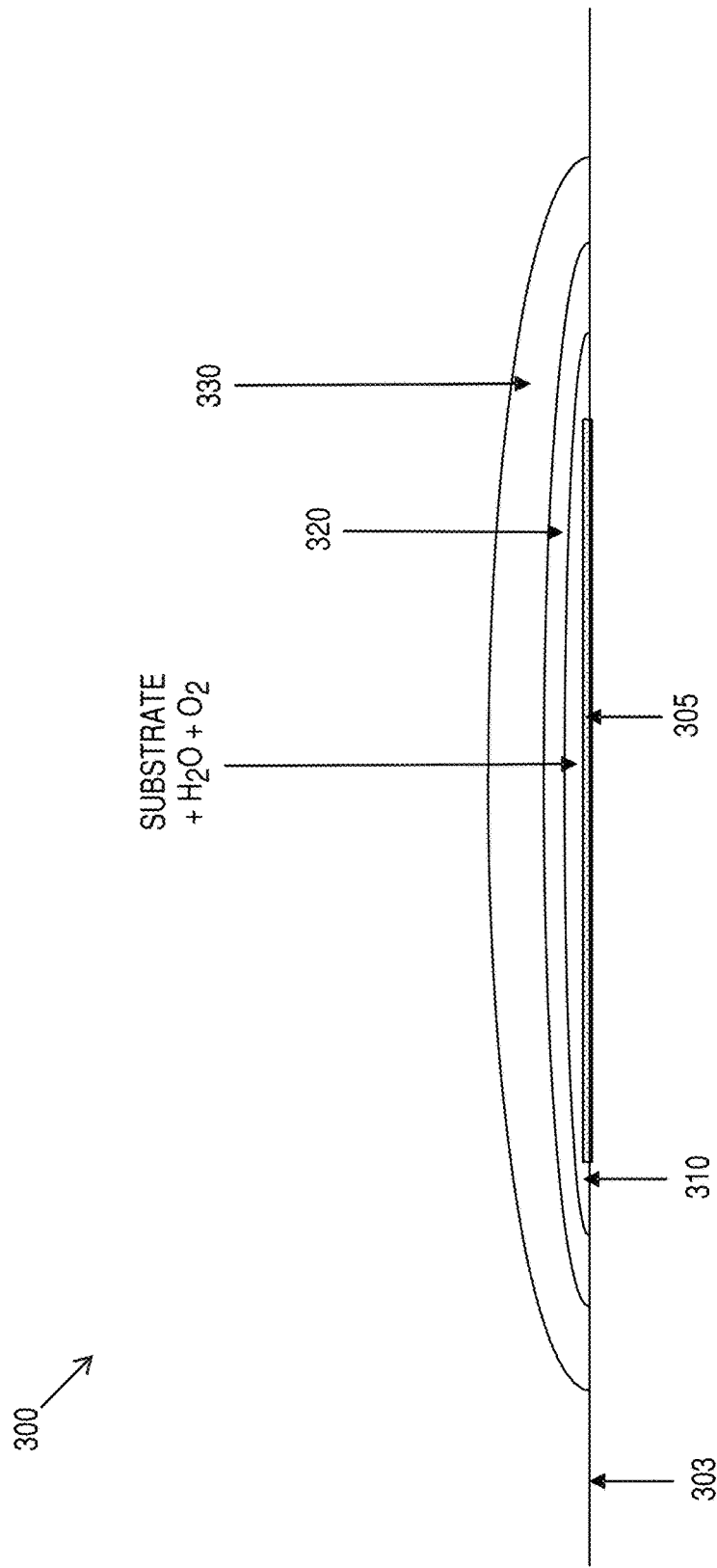
FIGS. 13 and 14 show processing steps and respective structures in accordance with some aspects of the present invention.

In alternative embodiments, the creatinine biosensor 300 may be modified as shown in FIG. 13 such that the biolayers 310, 320, and 330 are printed and/or dried in a high humidity environment, e.g., in the range of 40 to 98% RH. This process may result in the biolayers that have a substantially convex shape as shown in FIG. 13.

Figure 14:
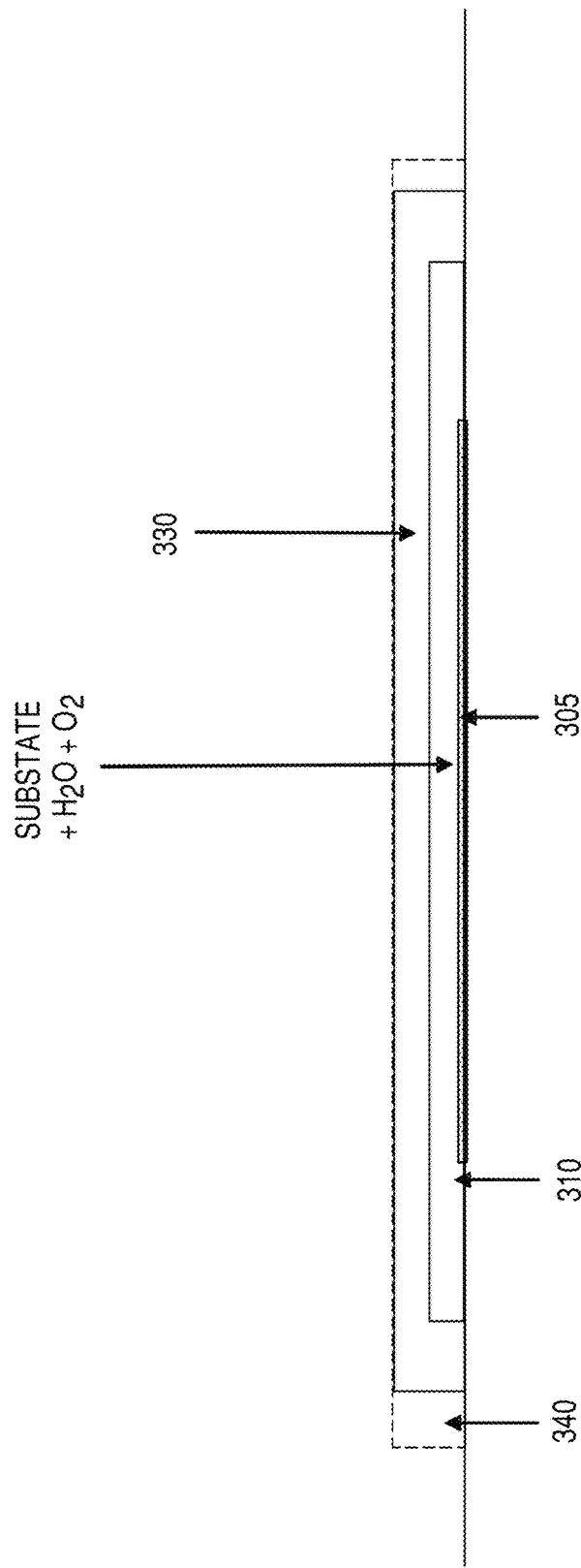
Figure 15:
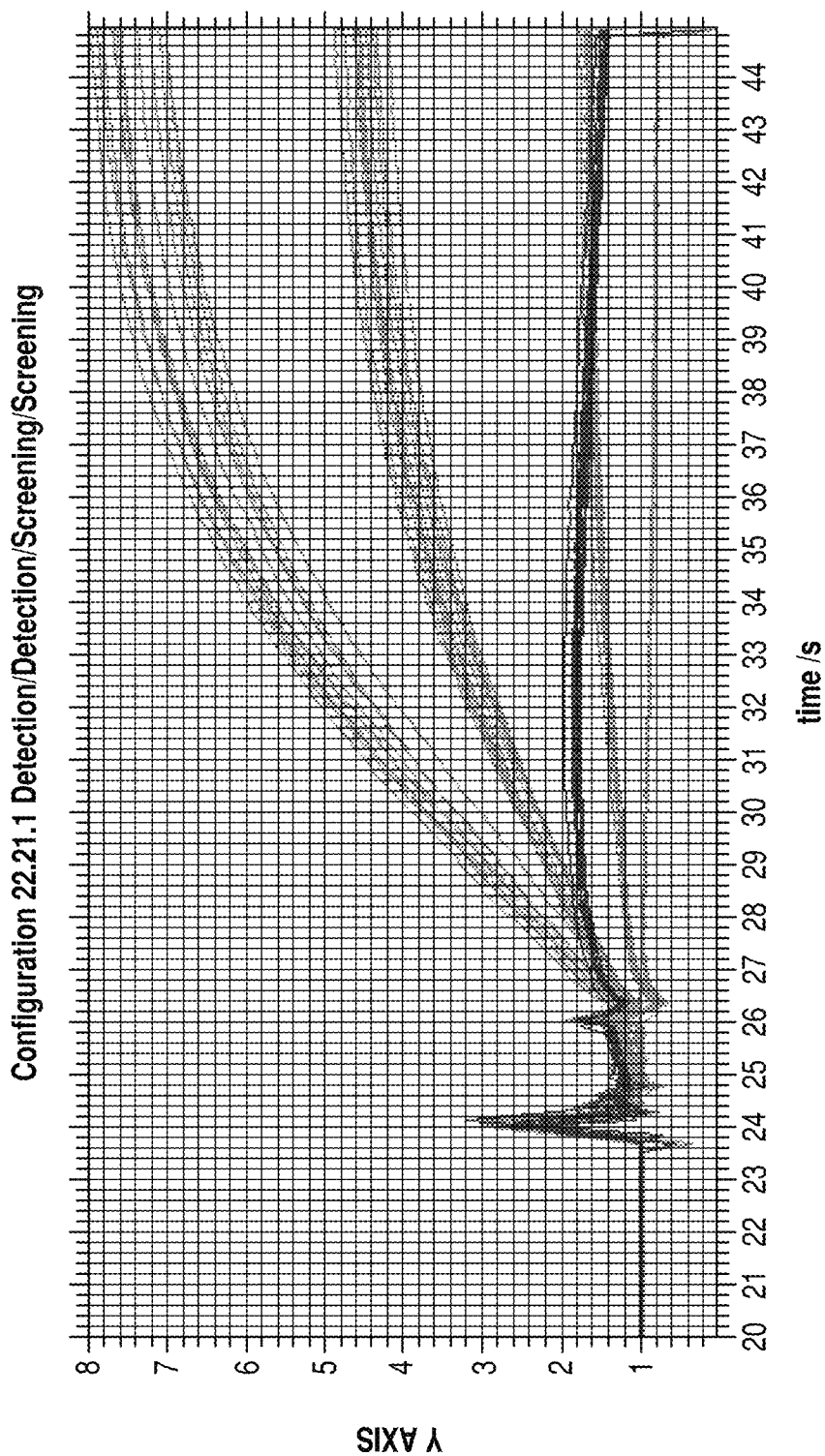
FIGS. 15 and 16 show creatinine related test data in accordance with some aspects of the invention.
Figure 16:
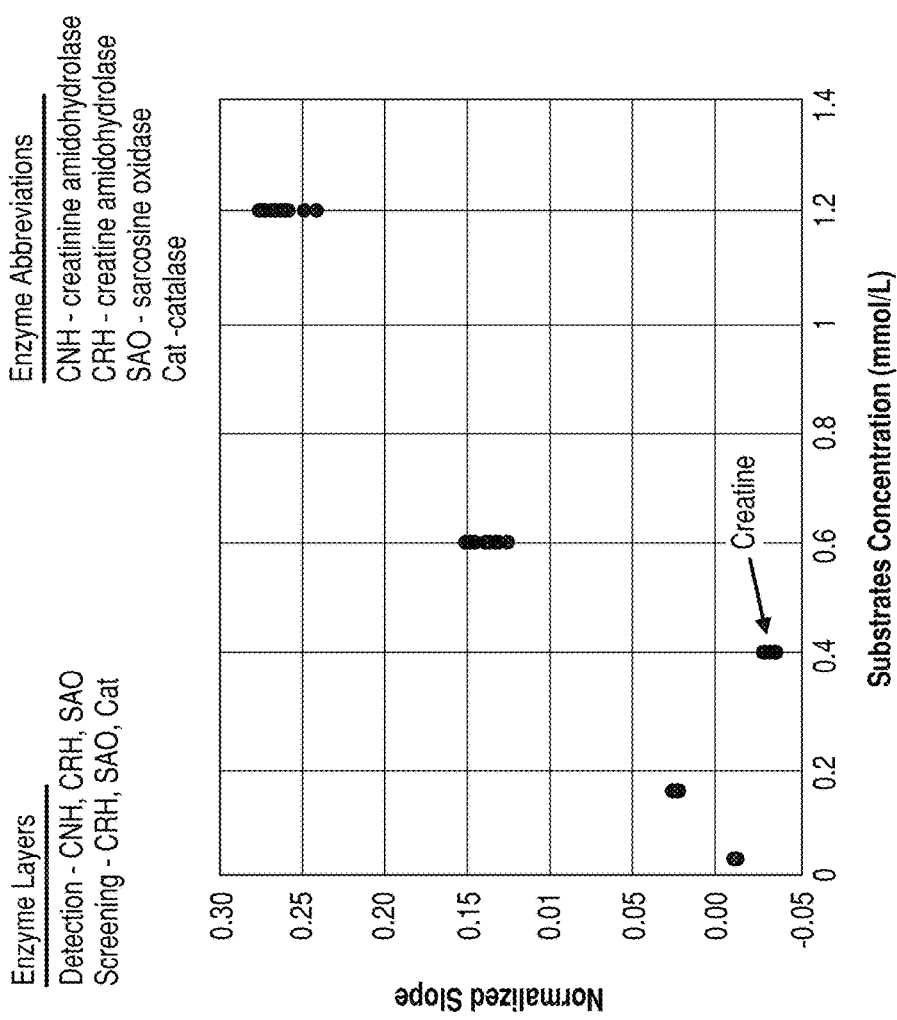

In alternative embodiments, the creatinine biosensor 300 may be modified to comprise only two biolayers as shown in FIG. 14. More specifically, biosensor 300 may be configured to only comprise a detection layer comprising CNH, CRH and SOX (e.g., biolayer 310) in various amounts and a screening layer comprising CRH, SOX and catalase (biolayer 330) in various amounts. Each biolayer may be produced by printing biolayer 310 twice and biolayer 330 twice as described above. FIG. 15 shows a response, in nanoamps of this alternative creatinine biosensor 300 to samples with various levels of creatinine (e.g., 0, 0.15, 0.6, 1.2 mmol/L). During the first 23 seconds, a calibrant solution is in contact with the creatinine biosensor 300, which is followed by the samples. The calibrant response (17-20 seconds) is taken just before the samples are put in front of the creatinine biosensor 300 and the sample signals are taken when the sample response is most stable (30-39 seconds). The sensor response may be normalized by dividing the slope of the sample response by the corresponding calibrant response of the sensor (DIV). FIG. 16 shows a plot of the DIV response for the various concentration of creatinine samples tested. This plot shows improved chemical removal of creatine interference and a reduced flux of creatine to the detection layer. Therefore, a lower detection signal (i.e., reduction of a positive interferent), however the loss of negative slope response for creatine may be achieved thereby appearing to give less creatine discrimination when using the slope of the sample signal as the analytical response.

Additional Structures for Use With the Aforementioned Microdispensing Processes

In alternative or additional embodiments, the creatinine biosensor 300 may be modified as shown in FIGS. 17-20 such that the biolayers 310, 320, and 330 are printed using additional structures or containment ring(s) to generate a predefined structure. The predefined structure may be configured to fabricate a lateral flow or vertical flow biosensor. The optional additional structure (e.g., containment ring 340) may be formed prior to dispensing the biolayers and configured to contain the drops of enzyme-hydrogel matrix. The additional structural component may be formed of a mask material such as a photoresist material that includes various viscosities such that it may be capable of sufficient sidewall definition and does not exhibit chemical incompatibility with the function of the biosensors structure. For example, in accordance with some aspects of the invention, a photoresist material may be selected that is an epoxy-based negative photoresist such as SU-8.

For example, as shown in FIGS. 17-20 the lateral flow biosensor 300 may comprise a base biosensor structure (e.g., wafer 303 and working electrode 305 fabricated as described above with respect to FIG. 3) and three biolayers (310, 320, and 330). The biosensor 300 may be fabricated using a printing process to stack the three biolayers one on top of the other inside containment rings 340 and 340'. More specifically, creatinine detection biolayer 310 may comprise CNH, CRH, and SOX such that the creatinine may be reduced to detectable hydrogen peroxide in the presence of a substrate that is free to diffuse through the multiple biolayers.

Figure 17:
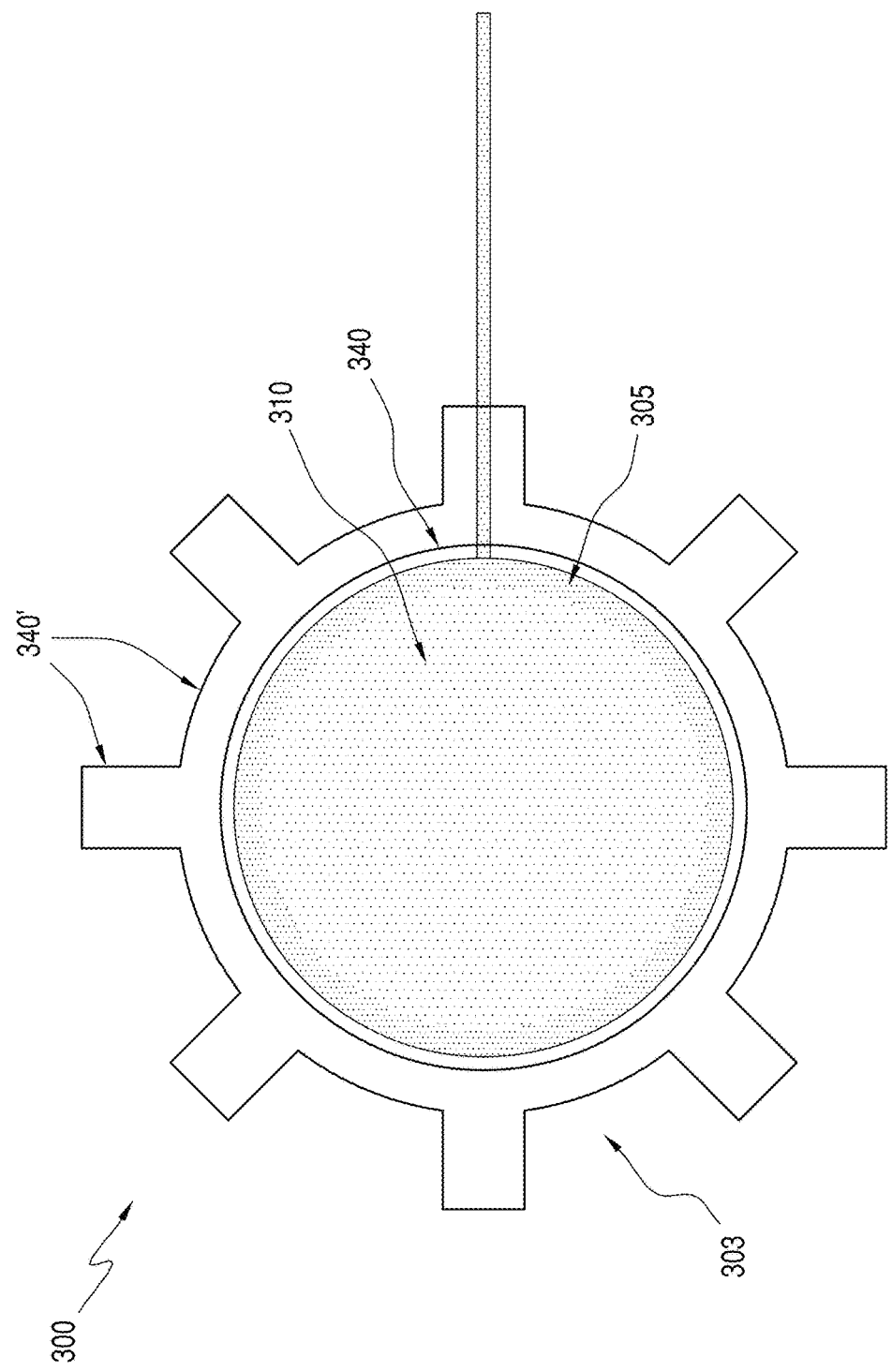
FIGS. 17-20 show processing steps and respective structures in accordance with some aspects of the present invention.
Figure 18:
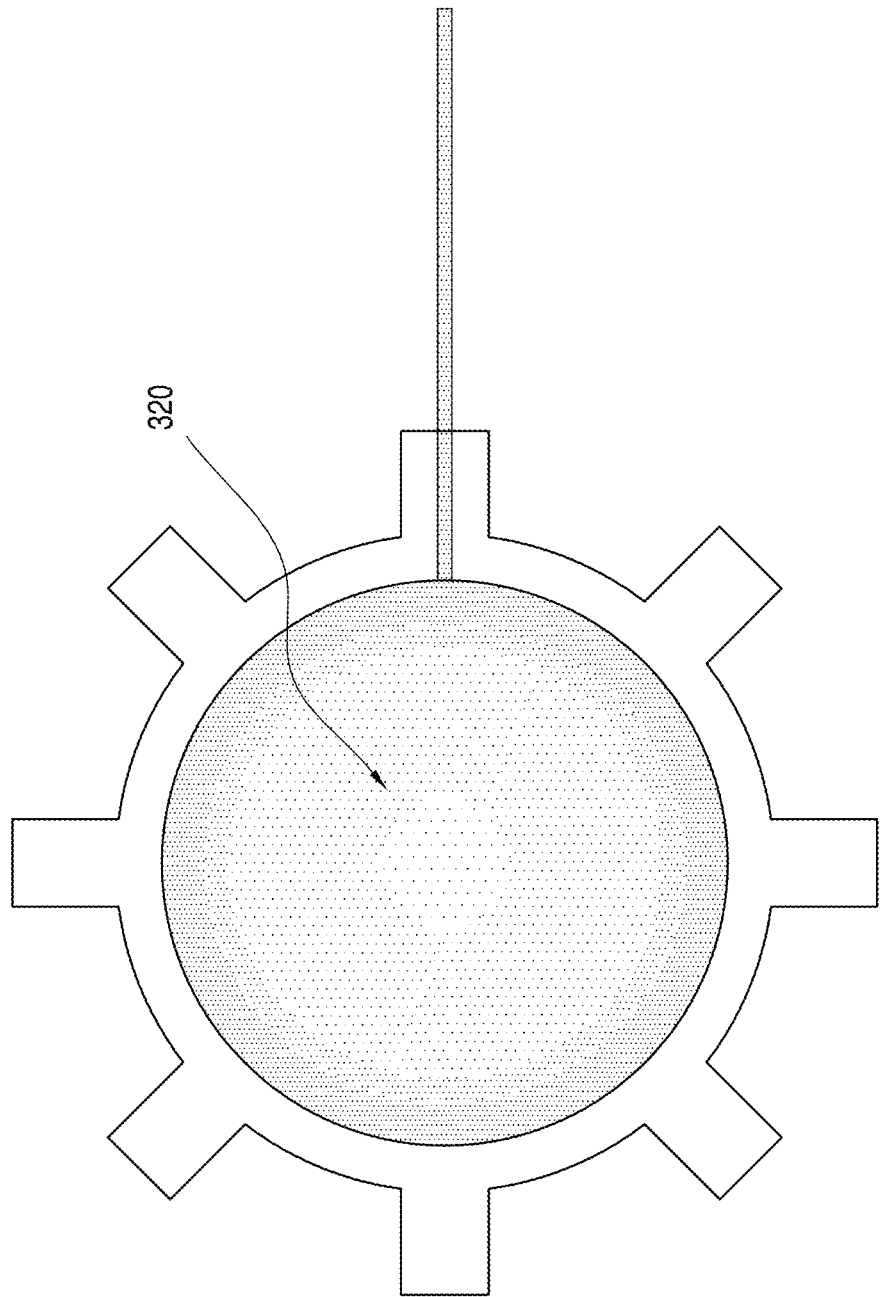
Figure 19:
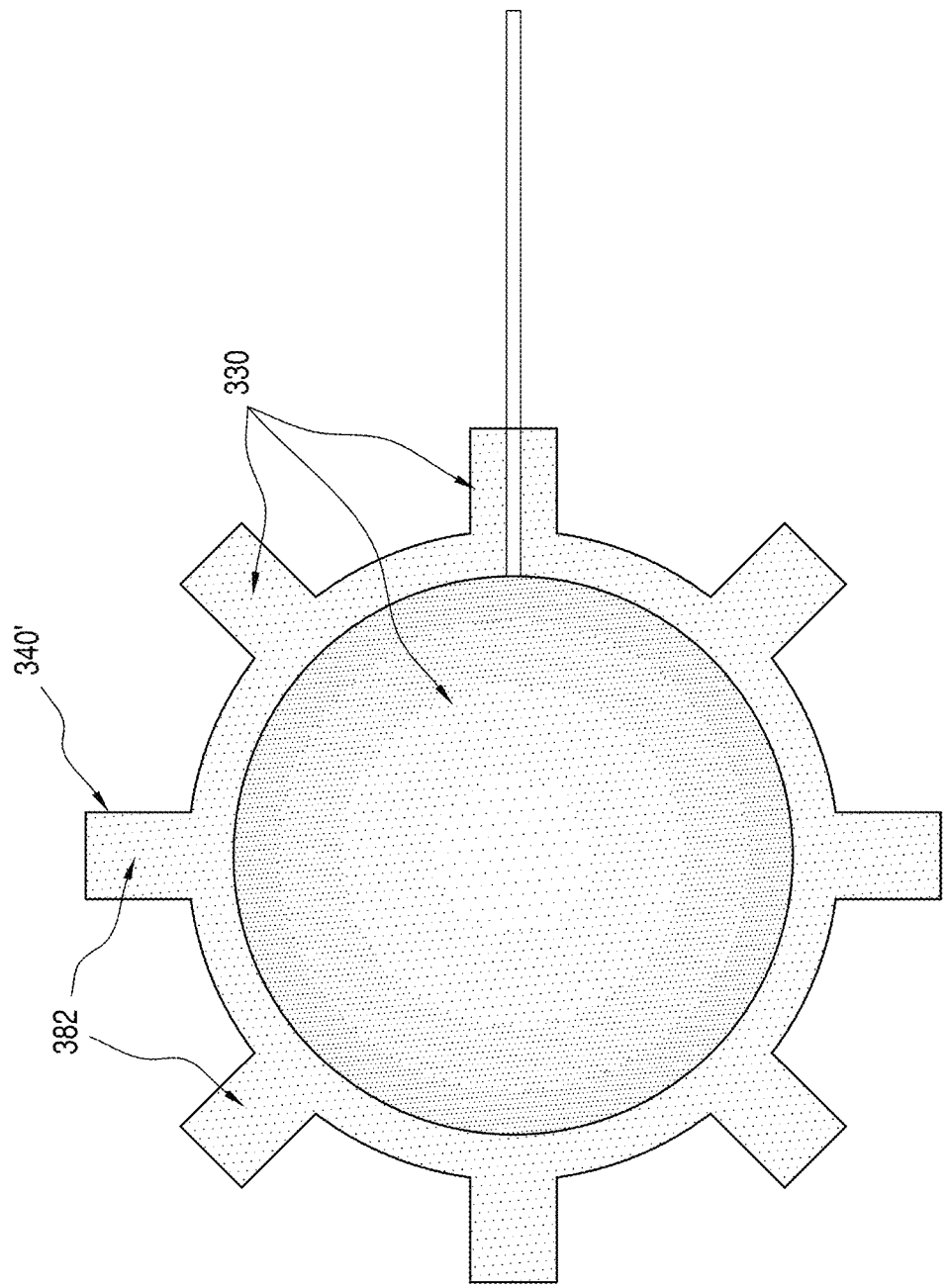
Figure 20:
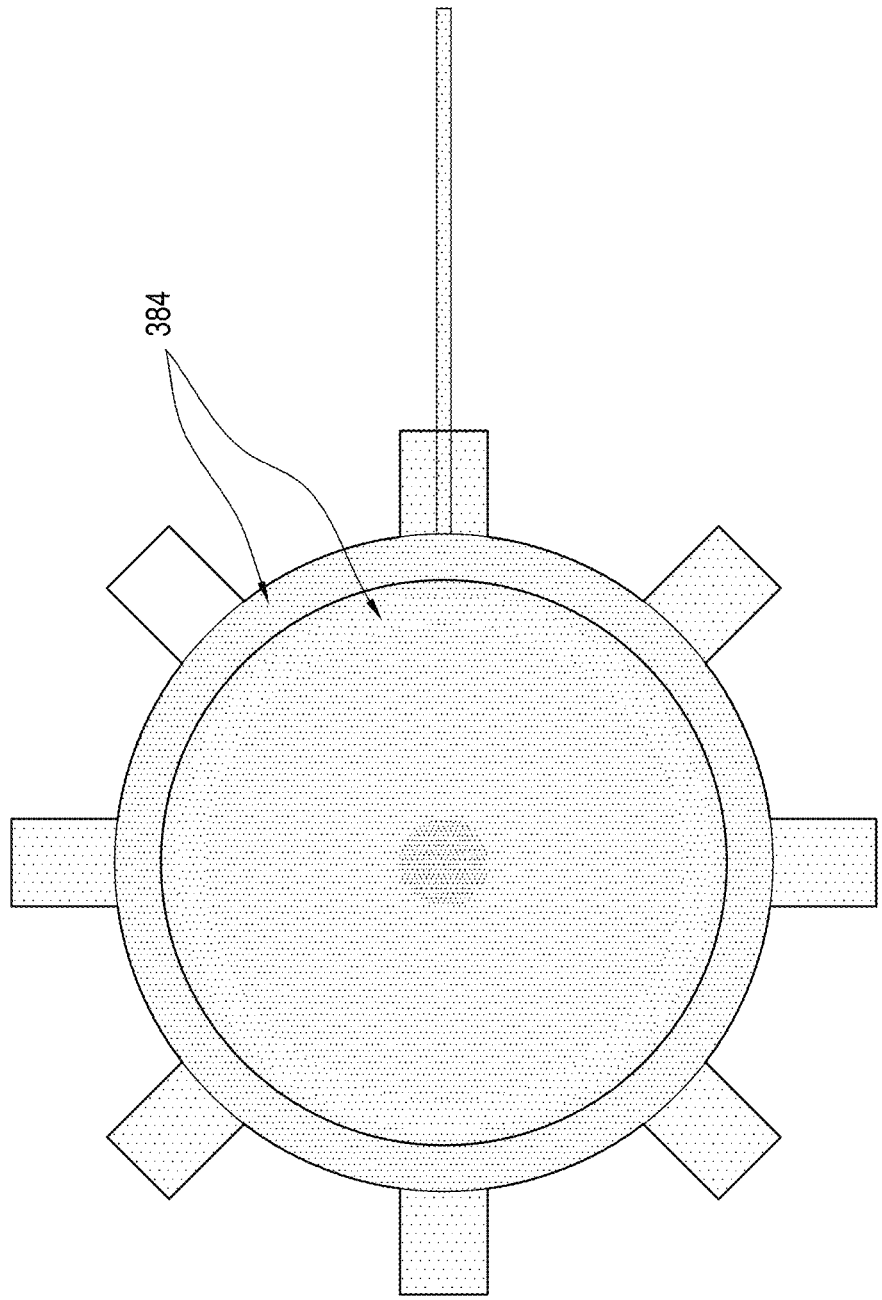

As shown in FIG. 17, the biolayer 310 may be formed within the containment ring 340 in accordance with similar processing steps used above with respect to biolayer 310 in FIGS. 8 and/or 13. Biolayer 320 may be configured as a diffusion biolayer comprising CRH such that the screening biolayer is separated from the creatinine detection biolayer 310. As shown in FIG. 18, the biolayer 320 may be formed within the containment ring 340 in accordance with similar processing steps used above with respect to biolayer 320 in FIGS. 8 and/or 13. Biolayer 330 may be configured as a screening biolayer comprising CRH, SOX and catalase such that creatine may be selectively screened from a sample. As shown in FIG. 19, the biolayer 330 may be formed within the containment ring 340' in accordance with similar processing steps used above with respect to biolayer 330 in FIGS. 8 and/or 13. For example, the biolayer 330 may extend into the tabs 382. As shown in FIG. 20, an additional impermeable layer 384 (e.g., a photo definable layer comprising methyl-silicone polycarbonate (MSP) hydrophobic polymer (Dow WL7154)) may be spin-coated or printed over the biolayer 330 in such a manner that the tabs 382 remain uncovered by the impermeable layer 384. Therefore, the tabs 382 may be act as wicks configured to contact the sample and permit the analyte to diffuse through the biolayers in a controlled and reproducible manner.

Systems Comprising a Biosensor Configured for Target Analyte Detection

Figure 21:
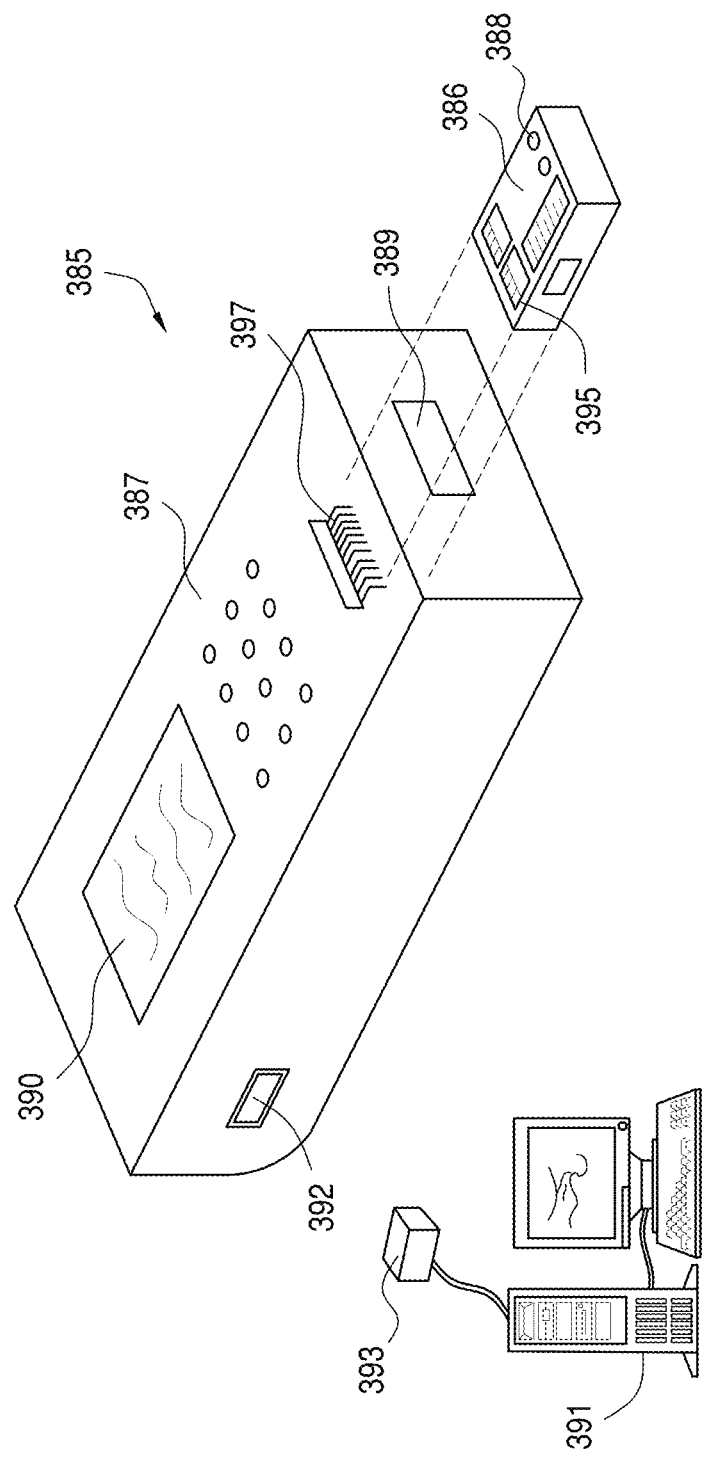
FIG. 21 shows an isometric view of a disposable sensing device and reader device in accordance with some aspects of the invention

Referring to FIG. 21, the system 385 of the present invention may comprise a self-contained disposable sensing device or cartridge 386 and a reader device or instrument 387. A fluid sample (e.g., whole blood or urine) to be measured is drawn into a sample entry orifice or port 388 in the cartridge 386, and the cartridge 386 may be inserted into the reader device 387 through a slotted opening 389. The reader device 387 may comprise a processor configured to perform measurements of analyte concentration within the fluid sample, as discussed herein in further detail. Measurements and determinations performed by the reader may be output to a display 390 or other output device, such as a printer or data management system 391 via a port on the reader 392 to a computer port 393. Transmission can be via Wifi, Bluetooth link, infrared and the like. Note that where the biosensors 395 are based on electrochemical principles of operation, the biosensors 395 in the cartridge 386 make electrical contact with the instrument 387 via an electrical connector 397. For example, the connector may be of the design disclosed in U.S. Pat. No. 4,954,087, incorporated herein by reference in its entirety. The instrument 387 may also include a method for automatic fluid flow compensation in the cartridge 386, as disclosed in U.S. Pat. No. 5,821,399, which also is incorporated herein by reference in its entirety.

Figure 22:
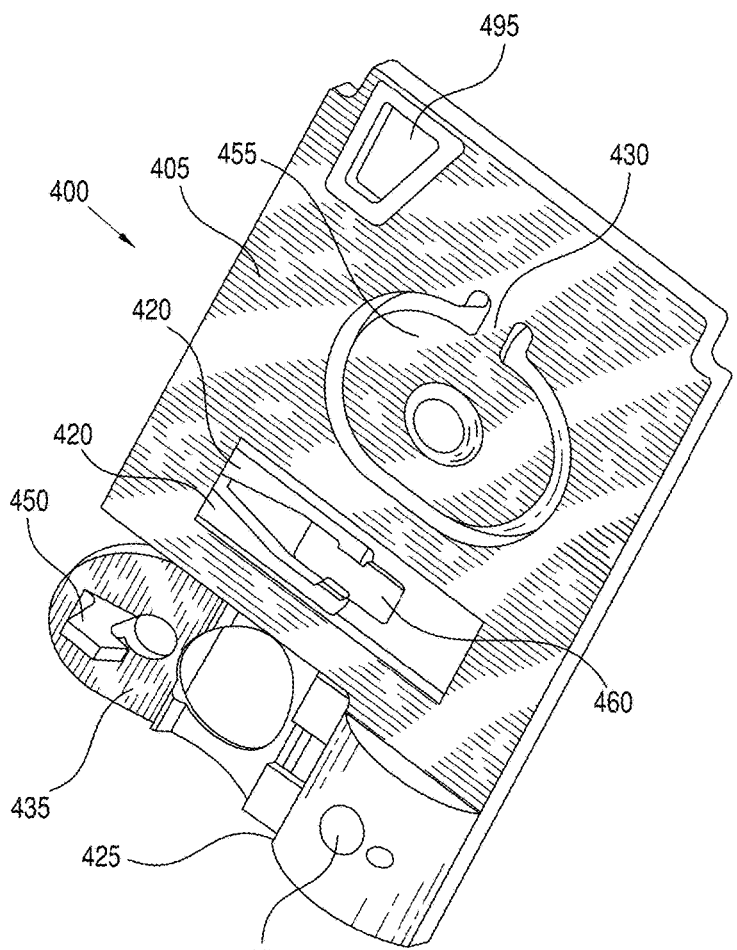
FIG. 22 shows an isometric top view of a cartridge cover in accordance with some aspects of the invention.
Figure 23:
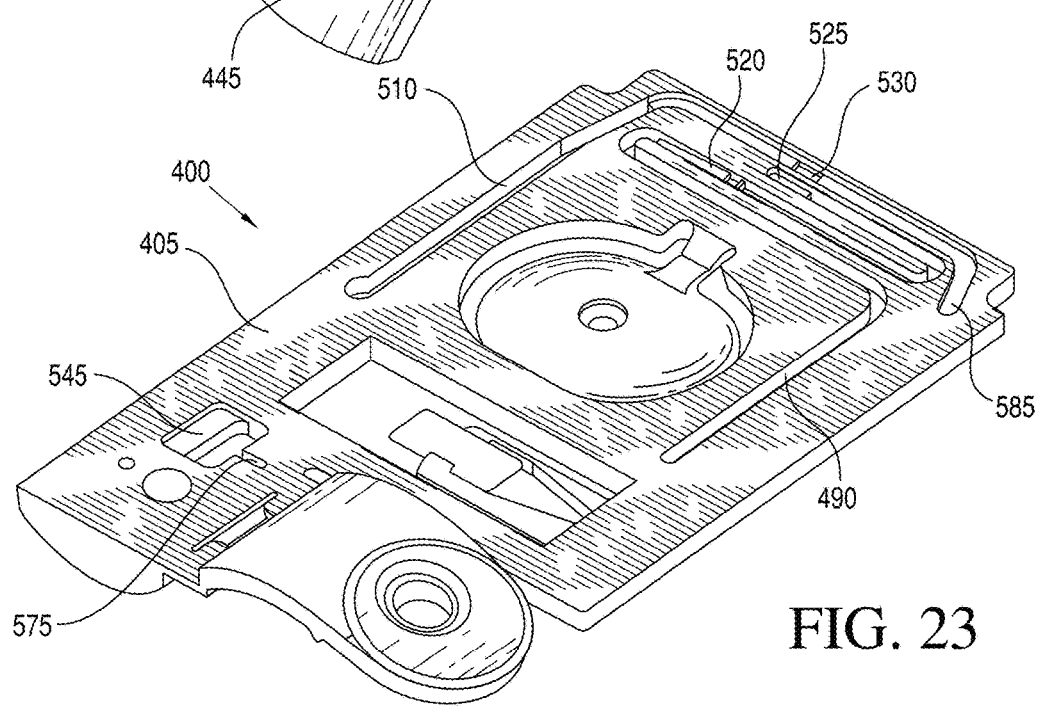
FIG. 23 shows an isometric bottom view of a cartridge cover in accordance with some aspects of the invention.
Figure 24:
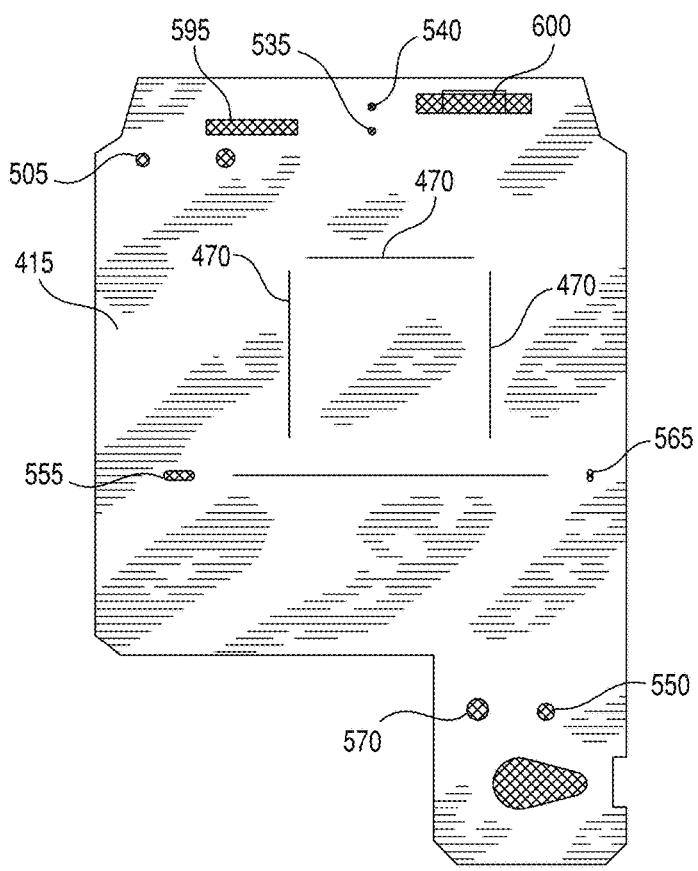
FIG. 24 shows a top view of a tape gasket in accordance with some aspects of the invention.
Figure 25:
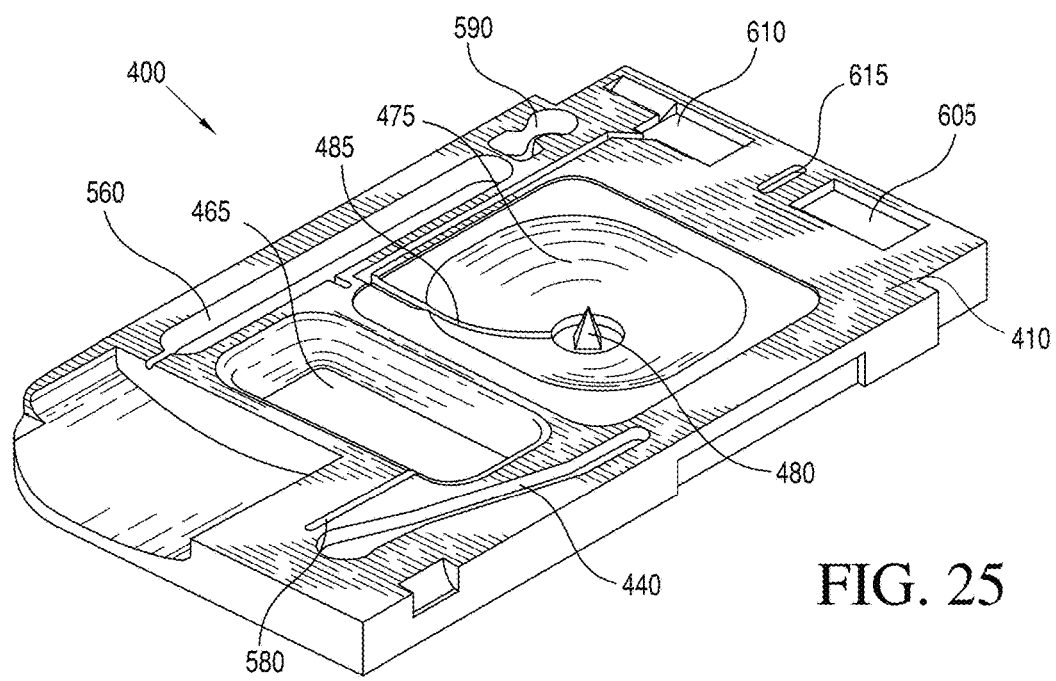
FIG. 25 shows an isometric top view of a cartridge base in accordance with some aspects of the invention.

In one embodiment, as shown in FIGS. 22-25, a cartridge 400 (e.g., a disposable assay cartridge) may comprise a cover 405 (as shown in FIGS. 22 and 23), a base 410 (as shown in FIG. 25), and a thin-film adhesive gasket 415 (as shown in FIG. 24) that is disposed between the base 410 and the cover 405. The cartridge 400 may be configured for insertion into a reader device, and therefore the cartridge 400 may comprise a plurality of mechanical and electrical connections (not shown) for this purpose. Advantageously, a feature of the cartridge 400 is that once a sample is loaded within the cartridge 400, analysis of the sample may be completed and the cartridge 400 may discarded without an operator or others contacting the sample.

Referring to FIG. 22, the cover 405 may be made of a rigid material, preferably plastic, and capable of repetitive deformation at flexible hinge regions 420, 425, and 430 without cracking. The cover 405 may comprise a lid 435, attached to a main body of the cover 405 by the flexible hinge 425. In operation, after introduction of a sample into a sample holding chamber 440 (as shown in FIG. 25) through a sample entry port 445, the lid 435 may be secured over an entrance to the sample entry port 445, preventing sample leakage. The lid 435 may be held in place by a hook 450.

The cartridge 400 optionally may also have a closure feature as described in U.S. Pat. No. 7,682,833, which is hereby incorporated by reference in its entirety, for sealing the sample entry port 445 in an air-tight manner. This closure device may be slidable with respect to a body of the cartridge 400 and provides a shearing action that displaces excess sample located in the region of the sample entry port 445, reliably sealing a portion of the sample in the sample holding chamber 440 between the sample entry port 445 and a capillary stop. Specifically, the cartridge 400 may be sealed by slidably moving a sealing element over the surface of the cartridge in a manner that displaces excess fluid sample away from the sample entry port 445, seals a volume of the fluid sample within the internal fluid sample holding chamber 440, and inhibits fluid sample from prematurely breaking through the internal capillary stop.

The cover 405 may further comprise two paddles 455 and 460 that are moveable relative to the body of the cover 405, and which are attached to the cover 405 by the flexible hinge regions 420 and 430. The paddle 460 may be configured to be operated by a pumping means such that a force is exerted upon an air bladder comprised of cavity 465 (as shown in FIG. 24) and the gasket 415. Operation of the paddle 460 displaces fluid within conduits of the cartridge 400.

The paddle 455 may be configured to be operated upon by a second pumping means such that a force is exerted upon the gasket 415, which can deform because of slits 470 cut therein (as shown in FIG. 24). Deformation of the gasket 415 may transmit pressure onto a fluid-containing foil pack filled with a fluid, e.g., approximately 130 μL of analysis/wash solution or fluid, located in cavity 475 (as shown in FIG. 25), rupturing the foil pack upon spike 480, and expelling fluid into conduit 485. The conduit 485 may be connected via a short transecting conduit in the base 410 to a conduit 490 (as shown in FIG. 23). The fluid fills a front of the conduit 485 first pushing fluid into a small opening in the gasket 415 that acts as a capillary stop.

Additional action in the cartridge 400 generated by mechanisms within the reading device applied to the cartridge 400 may be used to inject one or more air segments into the fluid at controlled positions within the conduit 490. The air segments may be used to wash the biosensor surface of the sensor array and the surrounding conduit 490 with a minimum amount of fluid. For example, the cover 405 may further comprise a hole covered by a thin pliable film 495. In operation, pressure exerted upon the film 495 may expel one or more air segments into the conduit 490 through a small hole 505 in the gasket 415 (as shown in FIGS. 23 and 24).

Referring to FIG. 23, a lower surface of the cover 405 further comprises the conduit 490 and another conduit 510. The conduit 490 includes a constriction 520 that controls fluid flow by providing resistance to the flow of the fluid. Optional coatings 525 and 530, e.g., dry reagent coatings, may provide hydrophobic surfaces on the conduit 510, which together with gasket holes 535 and 540 control fluid flow between conduits 190 and 510. A recess 545 in the base may provide a pathway for air to enter and/or escape the conduit 440 through hole 550 in the gasket.

Referring to FIG. 24, the thin-film gasket 415 comprises various holes and slits to facilitate transfer of fluid and air between conduits within the base 405 and the cover 410, and to allow the gasket 415 to deform under pressure where necessary. Specifically, a hole 555 may permit fluid to flow from the conduit 490 into a waste chamber 560, a hole 565 may comprise a capillary stop between conduits 440 and 510, a hole 570 may permit air to flow between a recess 575 (as shown in FIG. 23) and a conduit 580 (as shown in FIG. 24), the hole 550 provides for air movement between the recess 545 and the conduit 440, and the hole 505 permits fluid to flow from a conduit 585 (as shown in FIG. 23) to the waste chamber 560 via optional closeable valve 590 (as shown in FIG. 25). Holes 595 and 600 permit a plurality of electrodes that are housed within cutaways 605 and 610, respectively, to contact fluid within the conduit 490. In a specific embodiment, cutaway 610 houses a ground electrode, and/or a counter-reference electrode, and cutaway 605 houses at least one biosensor, and optionally, a reference sensor.

Referring to FIG. 25, the conduit 440 may be configured as a sample holding chamber that connects the sample entry port 445 to the conduit 510 in the assembled cartridge 400. The cutaway 605 may house at least one analyte biosensor, or an analyte responsive surface, together with an optional conductimetric sensor or sensors. The cutaway 610 may house a ground electrode if needed as a return current path for an electrochemical sensor, and may also house an optional conductimetric sensor. A cutaway 615 may provide a fluid path between gasket holes 535 and 540 such that fluid may pass between the conduits 490 and 510. Recess 475 houses a fluid-containing package, e.g., a rupturable pouch, in the assembled cartridge 400 that may be pierced by the spike 480 because of pressure exerted upon paddle 455 upon insertion of the cartridge 400 into the reading device. Fluid from the pierced package flows into the conduit 485. The air bladder may be comprised of the recess 465, which is sealed on its upper surface by the gasket 415. The air bladder may be one embodiment of a pump means, and may be actuated by pressure applied to the paddle 460, which displaces air in the conduit 580 and thereby displaces the sample from the sample chamber 440 into the conduit 510.

In some embodiments, a metering means may optionally comprise the sample chamber 440 bounded by the capillary stop 565 and having along the chamber 440 length an air entry point (gasket hole 550) from the bladder. Air pressure exerted at the gasket hole 550 drives a metered volume of the sample past the capillary stop 565. Therefore, a metered volume of sample may be predetermined by a volume of the sample chamber 440 between the air entry point 550 and the capillary stop 565. An amount of the sample corresponding to this volume may be displaced into the conduit 510 when the paddle 460 is displaced. This arrangement may therefore provide a metering means for delivering a metered amount of an unmetered sample into the various downstream conduits of the cartridge 400. The metering may be advantageous in some embodiments if quantitation of the analyte is required. Thus, an operator may be relieved of accurately measuring the volume of the sample prior to measurement saving time, effort, and increasing the accuracy and reproducibility.

Figure 26:
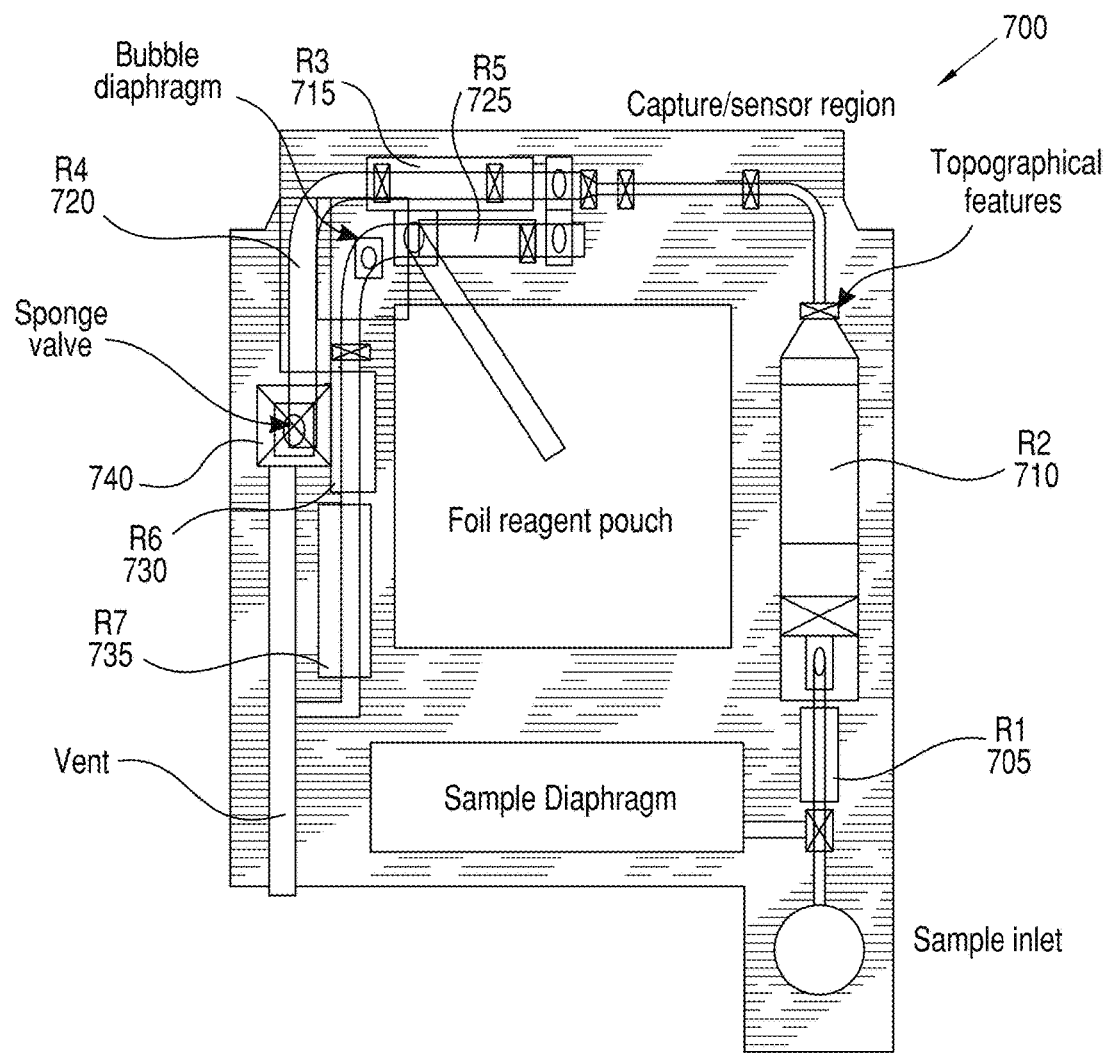
FIG. 26 shows a schematic view of the layout of a cartridge in accordance with some aspects of the invention.

As shown in FIG. 26, a schematic diagram of the features of the cartridge 700 and components therein is provided. Specifically, in preferred embodiments, the conduits and the sample chamber 705-735 may be coated with dry reagents to amend the sample or fluid as discussed herein. The sample or fluid may be passed at least once over the dry reagent to dissolve the dry reagent. Reagents that may be used to amend samples or fluid within the cartridge include enzymes, a water soluble protein, a buffer, scavengers, or combinations thereof, and/or blocking agents that prevent either specific or non-specific binding reactions among assay compounds. A surface coating that may not be soluble but helps prevent non-specific adsorption of assay components to the inner surfaces of the cartridge 700 may also be provided For example, within a segment of the sample or fluid, an amending substance may be preferentially dissolved and concentrated within a predetermined region of the segment. In one embodiment, this may be achieved through control of the position and movement of the segment within the conduits and the sample chamber 705-735. Therefore, if only a portion of a segment, such as the leading edge, is reciprocated over the amended substance, then a high local concentration of the substance can be achieved close to the leading edge. Alternatively, if a homogenous distribution of the substance is desired, for example if a known concentration of an amending substance is required for a quantitative analysis, then further reciprocation of the sample or fluid may result in mixing and an even distribution.

In preferred embodiments, a closeable valve 740 may be provided between a first conduit and the waste chamber. In one embodiment, the valve 740 may be comprised of a dried sponge material that is coated with an impermeable substance. In operation, contacting the sponge material with the sample or a fluid may result in swelling of the sponge to fill the cavity (e.g., the valve 590 cavity as shown in FIG. 25), thereby substantially blocking further flow of liquid into the waste chamber. Furthermore, the wetted valve 740 may also be configured to block the flow of air between the first conduit and the waste chamber, which permits a first pump means connected to the sample chamber to displace fluid within a second conduit, and to displace fluid from the second conduit into the first conduit in the following manner.

After the sample is exposed to the sensor array (e.g., the biosensors) for a controlled time, the sample may be moved into a post-analytical conduit where the sample may be amended with another reagent. The sample may then be moved back to the sensor array and a second reaction period may begin. Alternately, the post-analysis conduit may serve simply to separate the sample segment from the sensor array. Within the post-analysis conduit may be a single closeable valve that connects an air vent of the sensor conduit to a diaphragm air pump. When the single closeable valve closes, the sample may be locked in the post analytical conduit and cannot be moved back to the sensor array.

In a preferred embodiment of the present invention, the sample and a fluid, e.g., a combined wash and substrate delivery fluid, may contact the sensor array at different times during an assay sequence. The sample and the fluid may also be independently amended with other reagents or compounds present initially as dry coatings within respective conduits of a test device, e.g., the cartridge. Controlled motion of the fluid by the above-described pumping means within the cartridge further permits more than one substance to be amended into each fluid whenever the sample or the fluid is moved to a new region of the conduit. In this manner, multiple amendments to each fluid may be accommodated, extending the complexity of automated assays that can be performed in the cartridge. Therefore, the utility of the present invention may be enhanced.

In an alternative embodiment, as shown in FIGS. 27A-27E, the cartridge 900 may include a housing that comprises two complimentary halves of a cartridge (e.g., the cover 901 and the base 902), which can be bonded together to abut and attach the two complimentary interior surfaces of the two halves in a closed position. In some embodiments, the cover 901 and the base 902 are injection molded, for example, by machine as disclosed in U.S. patent application Ser. No. 13/530,501, filed on Jun. 22, 2012, which is incorporated herein by reference in its entirety. Preferably, the cover 901 is injection molded where a first substantially rigid zone 920 is formed in a first injection molding step and a substantially flexible zone 922 is formed in an additional injection molding step. Preferably, the base 902 is injection molded where a second substantially rigid zone 924 is formed in a first injection molding step.

As shown in FIGS. 27A-27E, the substantially rigid zones 920 and 924 of the cover 901 and the base 902, respectively, are preferably each a single contiguous zone; however, the molding process can provide a plurality of non-contiguous substantially rigid zones. The substantially flexible zone 922 is preferably a set of several non-contiguous zones. For example, the substantially flexible zone 922 around a displaceable membrane 925 may be separate and distinct from the substantially flexible zone at a closeable sealing member 928. Alternatively, the substantially flexible zone may comprise a single contiguous zone.

In a preferred embodiment, the cartridge housing comprises a sensor recess 930 in a portion of the substantially flexible zone. An advantage is that the sensors 935, which are disposed in the sensor recess 930 preferably are made on a silicon wafer substrate, which is relatively brittle. Thus, providing a substantially flexible sensor recess 930 results in a suitable support that can protect the sensor from cracking during assembly. Note that other non-silicon based sensors may be used, e.g., those made on a plastic substrate; however, the preferred embodiment uses sensors of the type described in U.S. Pat. Nos. 5,200,051; 5,514,253; and 6,030,827, the entireties of which are incorporated herein by reference. In addition to being substantially flexible, sensor recess 930 may be best selected to form a liquid-tight and/or air-tight seal around the sensor perimeter, thereby ensuring that liquids do not leak out of the conduit that covers the sensor in the fully assembled cartridge. In an alternative embodiment, sensor recess 930 can be formed in a portion of the substantially rigid zone (as shown in FIG. 25) of either or both of the cover or the bottom of the housing. In this aspect, a liquid-tight and/or air-tight seal optionally may be formed by the double-sided adhesive sheet 415 or gasket (as shown in FIG. 24).

With regard to overall dimensions, the preferred embodiment of the molded parts shown in FIGS. 27A-27E include the cover 901 with dimensions of about 6.0 cm×3.0 cm×0.2 cm and the base 902 with dimensions of about 5.0 cm×3.0 cm×0.2 cm to provide a cartridge 900 with dimensions of about 6.0 cm×3.0 cm×0.4 cm. In terms of ranges, the cartridge 900 optionally has a length of from 1 to 50 cm, e.g., from 5 to 15 cm, a width of from 0.5 to 15 cm, e.g., from 1 to 6 cm, and a thickness of from 0.1 to 2 cm, e.g., from 0.1 to 1 cm.

Processes for Target Analyte Detection Using a Biosensor

In preferred embodiments, the invention is a process for using a cartridge to determine the presence and/or concentration of a target analyte in a sample. The process may include introducing an unmetered fluid sample into the sample chamber 440 of the cartridge 400 through the sample entry port 445 (as shown in FIGS. 22-25). Capillary stop 565 prevents passage of the sample into conduit 510 at this stage, and conduit 440 is filled with the sample. Lid 435 is closed to prevent leakage of the sample from the cartridge. The cartridge may then be inserted into the reading device or apparatus 387, as shown in FIG. 21 and further disclosed in U.S. Pat. No. 5,821,399, which is incorporated herein by reference in its entirety. Insertion of the cartridge into the reading apparatus activates a mechanism, which punctures the fluid-containing package located at recess 475 when the package is pressed against spike 480. Fluid is thereby expelled into the conduits 485 and 490, arriving in sequence at the sensor region. The constriction 520 prevents further movement of fluid because residual hydrostatic pressure is dissipated by the flow of fluid via the conduit 585 into the waste chamber 560.

In a second step, operation of a pump means applies pressure to the air-bladder comprised of cavity 465, forcing air through the conduit 580 and into conduit 440 at a predetermined location. Capillary stop 565 delimits a metered portion of the original sample. While the sample is within sample chamber 440, it is preferably amended with a compound or compounds (e.g., enzymes, a water soluble protein, a buffer, scavengers, or a combination thereof) present initially as a dry coating or layer(s) on the inner surface of the chamber or conduits. The metered portion of the sample is then expelled through the capillary stop 565 by air pressure produced within air bladder comprised of cavity 465. The sample passes into the sensor conduit and into contact with the biosensor located within the cutaway 605.

To promote reaction of the analyte in the sample with the enzyme immobilized on or near the biosensor, the sample containing the analyte (e.g., creatinine) may optionally be passed repeatedly over the electrodes in an oscillatory motion. Preferably, the mode of operation is as described in jointly owned U.S. Pat. No. 5,096,669 which is incorporated by reference, where a calibrant fluid containing creatinine is first applied to the sensor and then the sample, e.g. blood, is moved over the sensor as the calibrant fluid is displace to a waste chamber.

Use of a cartridge with a closeable valve, preferably located between the sensor chamber and the waste chamber, is herein illustrated by a specific embodiment in which the concentration of creatinine is determined within a blood sample, which is introduced into the sample chamber of said cartridge. In the following time sequence, time zero (t=0) represents the time at which the cartridge is inserted into the cartridge reading device. Times are given in minutes. Between t=0 and t=1.5, the cartridge reading device makes electrical contact with the electrodes/sensors through pads, and performs certain diagnostic tests. Insertion of the cartridge perforates the foil pouch introducing calibrant fluid to the sensor. The diagnostic tests determine whether fluid or sample is present in the conduits using the conductivity electrodes; determine whether electrical short circuits are present in the electrodes; and ensure that the biosensor and ground electrodes are thermally equilibrated to, preferably, 37° C. prior to the analyte determination.

Various options exist for managing any temperature effect on an assay of this type. For example, the assay can be run in a system where the sample and other fluids and reagents are thermostated at a given temperature, e.g., 37° C. Alternatively, the assay may be run at ambient temperature, without any correction, or with correction to a standardized temperature based on measurement of the ambient value A metered portion of the sample, preferably between 4 and 200 μL, more preferably between 4 and 20 μL, and most preferably 7 μL, may be used to contact the electrodes/sensors as described above.

While the invention has been described in terms of various preferred embodiments, those skilled in the art will recognize that various modifications, substitutions, omissions and changes can be made without departing from the spirit of the present invention. It is intended that the scope of the present invention be limited solely by the scope of the following claims. In addition, it should be appreciated by those skilled in the art that a plurality of the various embodiments of the invention, as described above, may be coupled with one another and incorporated into a single reader device.

We claim:

1. A method of manufacturing a biosensor comprising:
   forming an electrode on a wafer;
   microdispensing a first matrix that includes creatinine amidohydrolase (CNH), creatine amidinohydrolase (CRH), and sarcosine oxidase (SOX) to form a first layer on the electrode;
   microdispensing a second matrix that includes CRH to form a second layer over the first layer; and
   microdispensing a third matrix that includes CRH, SOX, and catalase to form a third layer over the second layer such that the second layer is disposed between the first layer and the third layer,
   wherein the second layer completely covers the first layer,
   wherein the third layer completely covers the second layer, and
   wherein the second matrix and the third matrix are different.

2. The method of claim 1, wherein the first layer and the third layer are at least one of microdispensed and dried at a controlled humidity in a range of about 40-98% relative humidity.

3. The method of claim 1, further comprising, prior to forming the first layer, the second layer, and the third layer, forming a silane layer on the electrode such that the silane layer is disposed between the electrode and the first player.

4. The method of claim 1, further comprising, prior to forming the first layer, the second layer, and the third layer, forming a gamma amino silane layer on the electrode such that the gamma amino silane layer is disposed between the electrode and the first layer.

5. The method of claim 1, wherein a diameter of the electrode is less than a diameter of the first layer and a diameter of the second layer.

6. The method of claim 1, wherein a diameter of the first layer is less than or equal to a diameter of the second layer.

7. The method of claim 1, wherein the first matrix and the second third matrix are polymer matrixes.

8. The method of claim 1, wherein the first matrix and the third matrix are selected from the group consisting of: polyvinyl alcohol, gelatin, acrylamide, polyethyleneglycol diacrylate, or combinations thereof.

9. The method of claim 1, wherein the first matrix and the third matrix are photoformable.

10. The method of claim 1, wherein the first matrix and the third matrix comprise a photoinitiator.

11. The method of claim 10, wherein the photoinitiator is stilbazonium or dichromate.

12. The method of claim 1, wherein the first layer, the second layer, and the third layer comprise a substantially concave shape.

13. The method of claim 1, wherein the first layer, the second layer, and the third layer comprise a substantially convex shape.

14. A method of manufacturing a biosensor comprising:
    forming an electrode on a wafer;
    printing a first layer on a top surface the electrode, the first layer comprising creatinine amidohydrolase (CNH), creatine amidinohydrolase (CRH), and sarcosine oxidase (SOX);
    printing a second layer on a top surface of the first layer, the second layer comprising CRH and having a composition different from that of the first layer; and
    printing a third layer on a top surface of the second layer such that the second layer is disposed between the first layer and the third layer, the third layer comprising CRH, SOX, and catalase and having a composition different from the second layer.

* * * * *